United States Patent
Matthews et al.

(10) Patent No.: US 6,464,971 B1
(45) Date of Patent: Oct. 15, 2002

(54) ANIONIC OR CATIONIC DENDRIMER ANTIMICROBIAL OR AUTIPROTOZOAN COMPOSITIONS

(75) Inventors: Barry Ross Matthews, Olinda; George Holan, Brighton, both of (AU)

(73) Assignee: Starpharma Limited, Parkville (AU)

(*) Notice: Subject to any disclaimer, the term of this patent is extended or adjusted under 35 U.S.C. 154(b) by 0 days.

(21) Appl. No.: 09/786,913
(22) PCT Filed: Sep. 13, 1999
(86) PCT No.: PCT/AU99/00763
§ 371 (c)(1), (2), (4) Date: May 8, 2001
(87) PCT Pub. No.: WO00/15240
PCT Pub. Date: Mar. 23, 2000

(30) Foreign Application Priority Data

Sep. 14, 1998 (AU) .............................. 5842/98

(51) Int. Cl.[7] ...................... A61K 31/785; A61P 31/04; A61P 31/10; A61P 33/02; C08G 73/00
(52) U.S. Cl. .................. 424/78.17; 424/78.27; 424/78.29; 424/DIG. 16; 424/405; 525/540
(58) Field of Search .............. 424/78.17, 464, 424/489, 423, 78.27, 78.29, DIG. 16; 514/61; 525/512, 513, 514

(56) References Cited

U.S. PATENT DOCUMENTS 5,736,533 A * 4/1998 Simon et al. ................. 514/61
6,190,650 B1 * 2/2001 Matthews et al. .......... 424/78.1

FOREIGN PATENT DOCUMENTS

| WO | 95/34595 | 12/1995 |
| WO | 97/14404 | 12/1997 |
| WO | 97/48711 | 12/1997 |
| WO | 98/26662 | 6/1998 |

OTHER PUBLICATIONS

Attia et al., "Interaction of Oligodeoxynucleotides with Mycobacteria: Implications for New Therapeutic Strategies," *Antisense & Nucleic Acid Drug Development*, 1998, vol. 8, pp. 207–214, Mary Ann Liebert, Inc.

* cited by examiner

*Primary Examiner*—Edward J. Webman
*Assistant Examiner*—Helen Nguyen
(74) *Attorney, Agent, or Firm*—Foley & Lardner

(57) ABSTRACT

To inhibit, prophylactically or therapeutically, a bacterial, yeast, fungal, or parasitic agent in a patient, an effective amount of a dendrimer is administered to the patient, which dendrimer has a plurality of terminal groups, at least one of which has an anionic- or cationic-moiety covalently bonded or linked thereto. The anionic-containing moiety is not a disaccharide or oligosaccharide moiety, and, where the anionic-containing moiety is a neuraminic- or sialic acid-containing. moiety, it is modified in the 4-position by substitution with an amino, amido, cyano, azido or guanido group, or is unsaturated.

12 Claims, 5 Drawing Sheets

Effect of BRI-6181 on growth of *P. falciparum* in human red blood cells *in vitro*.

—○— Control    —▲— 10μg/ml BRI-6181
—■— 25μg/ml BRI-6181    —●— 50μg/ml BRI-6181

PRBC= Parasitised Red Blood Cells

T = Trophozoites  R = Rings  S = Schizonts.
Indicates the stage of maturity of the majority of parasites in control wells.

Effect of BRI-2999 on growth of *P. falciparum* in human red blood cells *in vitro*.

T = Trophozoites  R = Rings  T/S = Trophozoites or Schizonts
PRBC=parasitised red blood cells Effect of BRI-6741 on growth of *P. falciparum* in human red blood cells *in vitro*.

PRBC=Parasitised Red Blood Cells

T = Trophozoites  R = Rings  S = Schizonts.
Indicates the stage of maturity of the majority of parasites in control wells.

Effect of BRI-2998 on growth of *P. falciparum* in human red blood cells *in vitro*.

PRBC=Parasitised Red Blood Cells

T = Trophozoites  R = Rings  S = Schizonts.
Indicates the stage of maturity of the majority of parasites in control wells.

Effect of BRI-7011 on growth of *P. falciparum* in human red blood cells *in vitro*.

PRBC=Parasitised Red Blood Cells

T = Trophozoites  R = Rings  S = Schizonts.
Indicates the stage of maturity of the majority of parasites in control wells.

Effect of BRI-6181 on growth of *P. falciparum* in human red blood cells *in vitro*.

PRBC= Parasitised Red Blood Cells

T = Trophozoites  R = Rings  S = Schizonts.
Indicates the stage of maturity of the majority of parasites in control wells.

ANIONIC OR CATIONIC DENDRIMER ANTIMICROBIAL OR AUTIPROTOZOAN COMPOSITIONS

FIELD OF THE INVENTION

This invention relates to inhibition of microbial and parasitic agents, and in particular it relates to the use of dendrimers as inhibitors of infection of human and non-human animal patients by pathogens such as bacteria, fungi or parasites.

BACKGROUND OF THE INVENTION

Dendrimers are 3-dimensional polymeric materials of low polydispersity which are characterised by a large number of surface terminal groups. In addition, the manner in which these materials are prepared allows tight control over the size, shape, and number and type of surface groups. Dendritic materials have several features that are useful for use as therapeutic materials: fixed shape which presents a large and defined surface with which to interact with biological surfaces and receptors; and the large number of terminal groups allow for multiple interactions with the biological targets.

International Patent Applications No. PCT/AU95/00350 (WO 95/34595) and PCT/AU97100447 (WO 98/03573) disclose dendrimers such as a polyamidoamine or polylysine dendrimers having a plurality of terminal groups, wherein at least one of the terminal groups has an anionic- or cationic-containing moiety bonded or linked thereto. The contents of these published International patent applications are incorporated herein by reference.

The present invention provides the use of dendritic polymers in the inhibition of microbial agents including bacterial and fungal pathogens, and parasitic agents.

SUMMARY OF THE INVENTION

According to the present invention, there is provided a method of prophylactic or therapeutic inhibition of a microbial or parasitic agent in a human or non-human animal patient, which comprises administration to the patient of an effective amount of a dendrimer having a plurality of terminal groups wherein at least one of said terminal groups has an anionic- or cationic-containing moiety bonded or linked thereto.

Particularly preferred compounds for use in the method of the present invention are dendrimers having sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid; primary, secondary, tertiary or quaternary amino-containing moieties, pyridinium-containing moieties; guanidinium-containing moieties; amidinium-containing moieties; phenol-containing moieties; heterocycles possessing acidic or basic hydrogens; zwitterionic-containing moieties; or mixtures of the above moieties, linked to terminal groups thereof.

The compounds used in the method of this invention are referred to herein as polyionic dendrimers, and this term is used throughout this specification to include not only the dendrimers per se, but also their pharmaceutically or veterinarily acceptable salts, for example the alkaline metal or alkaline earth metal salts such as the sodium, potassium or calcium salts as well as pharmaceutically acceptable anions such as fluoride, chloride, bromide, iodide, citrate, acetate, p-toluene sulfonate and the like.

DETAILED DESCRIPTION OF THE INVENTION

Preferred compounds used in accordance with the present invention include polyionic dendrimers of the general formula I:

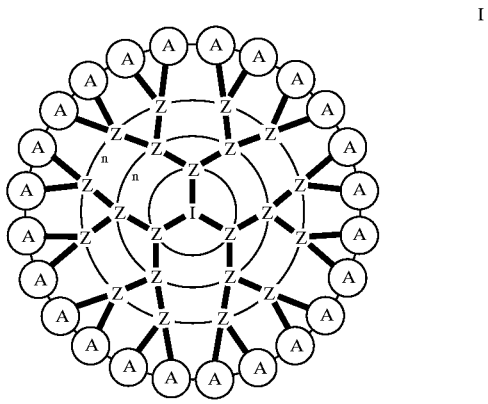

wherein: I is an initiator core;
Z is an interior branching unit;
n is an integer which represents the number of generations of the dendrimer; and
A is an anionic- or cationic-containing moiety which may be linked to interior branching unit Z through an optional linking group X.

Dendrimers are macromolecular highly branched compounds formed by reiterative reaction sequences starting from an initial core molecule with successive layers or stages being added in successive "generations" to build up a three-dimensional, highly ordered polymeric compound. Dendrimers are characterised by the following features: I an initator core (I) which may have one or more reactive sites and be point-like or of significant size so as to effect the final topology of the dendrimer; ii layers of branched repeating units (Z) attached to the initiator core; iii functional terminal groups (such as moieties A) attached to the surface of the dendrimer, optionally through linking groups (such as linking groups X). The present invention uses dendritic structures as frameworks for the attachment of ionic moieties; the invention is not limited to the spherical dendrimers described in detail herein but can be based on any dendritic structure. The variety of dendrimers in both shape and constitution are well known to persons skilled in the art.

The preparation of dendrimers is well known, and is described by way of example in U.S. Pat. Nos. 4,289,872 and 4,410,688 (describing dendrimers based on layers of lysine units), as well as U.S. Pat. Nos. 4,507,466, 4,558,120, 4,568,737 and 4,587,329 (describing dendrimers based on other units including polyamidoamine or PAMAM dendrimers). The dendrimers disclosed in these U.S. patents are described as being suitable for uses such as surface modifying agents, as metal chelating agents, as demulsifiers or oil/water emulsions, wet strength agents in the manufacture of paper, and as agents for modifying viscosity in aqueous formulations such as paints. It is also suggested in U.S. Pat. Nos. 4,289,872 and 4,410,688 that the dendrimers based on lysine units can be used as substrates for the preparation of pharmaceutical dosages.

International Patent Publications Nos. WO 88/01178, WO 88/01179 and WO 88/01180 disclose conjugates in which a dendrimer is conjugated or associated with another material such as a carried pharmaceutical or agricultural material. In addition, International Patent Publication No. WO 95/24221 discloses dendritic polymer conjugates composed of at least one dendrimer in association with a carrier material which can be a biological response modifier, and optionally a target director. These patent publications together with the U.S. patents mentioned above contain a broad disclosure of various dendrimers and processes for the preparation thereof, and the disclosure of each of these publications is incorporated herein by reference.

The term "dendrimer" as used herein is to be understood in its broadest sense, and to include within its scope all forms and compositions of these dendrimers as disclosed in Patent Publications Nos. WO 88/01178, WO 88/01179 and WO 88/01180. The term also includes linked or bridged dendrimers as disclosed in these patent publications.

The preferred dendrimers of the present invention comprise a polyvalent core covalently bonded to at least two dendritic branches, and preferably extend through at least two generations. Particularly preferred dendrimers are polyamidoamine (PAMAM) dendrimers, PAMAM (EDA) dendrimers, poly(Propyleneimine) (PPI) dendrimers and polylysine dendrimers.

In accordance with the present invention, at least one, and preferably a substantial number, of the terminal groups on the surface of the dendrimer has an anionic- or cationic-containing moiety covalently bonded thereto. The branches of the dendrimer may terminate in amino groups or other functional reactive groups such as OH, SH, or the like, which subsequently can be reacted with the anionic or cationic moieties. Where the terminal groups of the dendrimer are amine groups, the anionic- or cationic-containing moiety may be linked to the dendrimer by a variety of functional groups including amide and thiourea linkages. Preferred anionic- or cationic-containing moieties which may be bonded to the terminal groups of the dendrimer include sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties) and primary, secondary, tertiary or quaternary amino-containing moieties, pyridinium-containing moieties; guanidinium-containing moieties; amidinium-containing moieties; phenol-containing moieties; heterocycles possessing acidic or basic hydrogens; zwitterionic-containing moieties; or mixtures of the above moieties.

Suitable anionic- and cationic-containing moieties which may be bonded or linked to the amino or other terminal groups include, by way of example, the following groups (in which n is zero or a positive integer, more particularly n is zero or an integer of from 1 to 20):

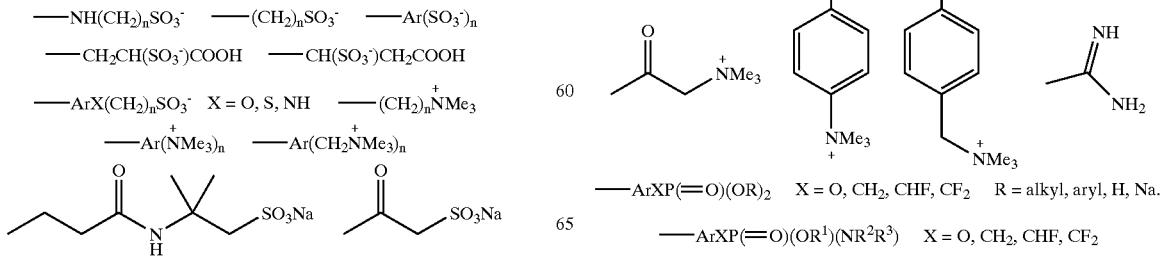

-continued $R^1$ = alkyl, aryl, H, Na   $R^2, R^3$ = alkyl, aryl

—Ar[P(=O)(OR)$_2$]$_n$   R = alkyl, aryl, H, Na   n = 1–3

—Ar[B(OH)$_2$]$_n$   n = 1–3   —Ar[COOH]$_n$   n = 1–3

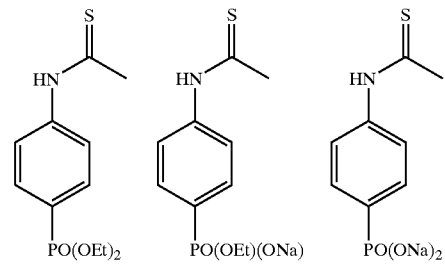

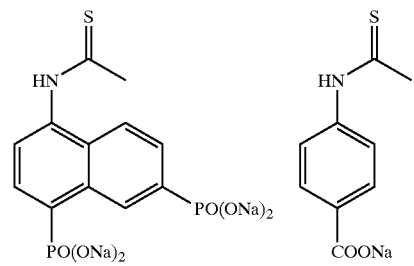

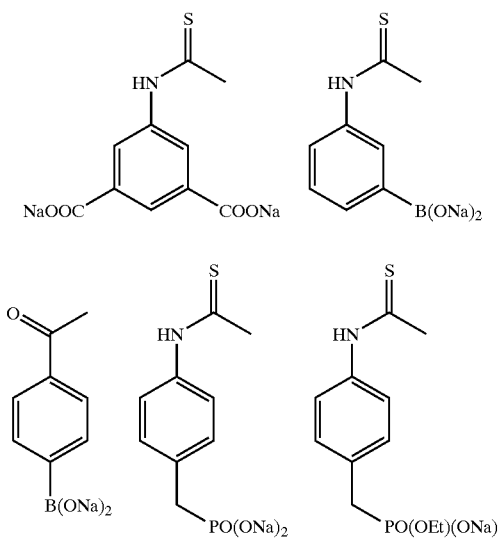

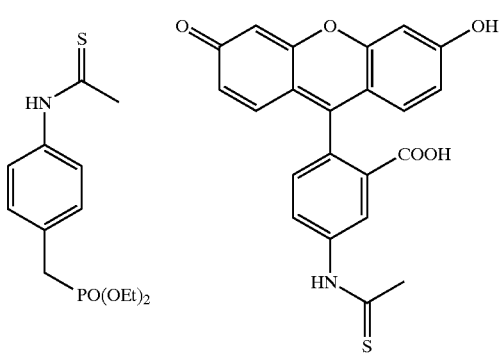

-continued

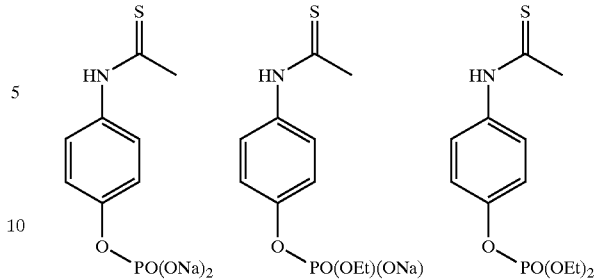

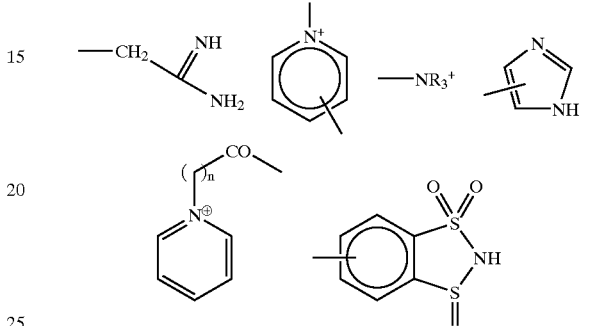

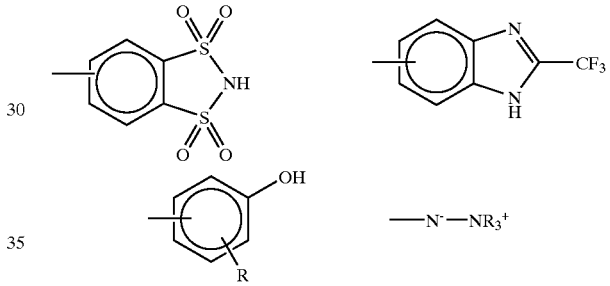

R = alkyl or arylalkyl; $R_1$, $R_2$, $R_3$ (which may be same or different) = alkyl or arylalkyl

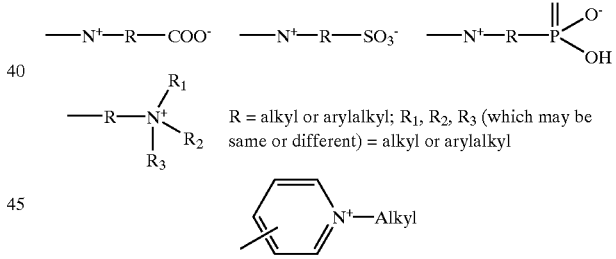

In addition to the above, various neuraminic or sialic acid-containing moieties or modified neuraminic or sialic acid-containing moieties may be bonded or linked to the dendrimers in accordance with this invention. These moieties include the various N- and O-substituted derivatives of neuraminic acid, particularly N- and O-acyl derivatives such as N-acetyl, O-acetyl and N-glycolyl derivatives, as well as moieties in which the neuraminic acid group is modified. Suitable modified neuramine acid groups include groups which are substituted in the 4-position with an amino, amido, cyano, azido or guanidino group, as well as unsaturated neuraminic acid groups. These moieties may be linked to the dendrimers through the 2-, 7-, 9- or 5-NAc positions.

Preferably, in the polyionic dendrimers of the general formula I, n is an integer of from 1 to 20 or more, more preferably from 1 to 10. Preferably also, the dendrimers include at least three or more terminal groups.

The optional linking group X which may be present to act as a spacer between the dendrimer and the moiety A, may consist of an alkyl chain (optionally substituted or branched), an alkoxy, polyalkoxy, alkylthio or polyalkylthio chain (optionally substituted), or an alkenyl, multiple alkenyl, alkynyl or multiple alkynyl chain (optionally substituted). Suitable spacer chains include groups of the formula —$(CH_2)_m$—Z—$(CH_2)_m$—, wherein Z is —$CH_2$—, —CH=CH—, —C≡C—, —O— or —S— and m is an integer of from 1 to 15.

The anionic or cationic dendrimers of this invention may be prepared by standard chemical methods which are well known to persons skilled in this art. Suitable methods are described by way of the example in Examples below.

As previously described, the anionic or cationic dendrimers of the present invention have been found to inhibit microbial and parasitic agents. The term "microbial agent" as used herein is intended to refer to both bacterial and yeast or fungal agents, particularly bacterial and yeast or fungal pathogens. Thus, the term includes, but is not limited to, Gram-positive and Gram-negative bacteria such as *Eschericia coli, Salmonella typhimurium*, and Streptococcus, Staphylococcus, Shigella, Pseudomonas, Clostridium, Neisseria and Pneumococcus species. In addition, this term includes yeast pathogens such as Candida and fungal pathogens such as *Aspergillus fumigatus*.

The term "parasitic agent" is used herein to refer in particular to parasitic pathogens, including but not limited to parasitic agents such as Plasmodium, Trypanosoma and Leischmania species, *Toxoplasma gondii, Pneumocystis carinii* and *Criptosporidium parvum*.

The term "inhibition" is used herein in its broadest sense to include either full or partial inhibition or suppression of infection of a human or non-human animal patient by a microbial or parasitic pathogen, or full or partial inhibition or suppression of the pathogenic effects of infection of such a patient by a microbial or parasitic pathogen. The term is also used to encompass both prophylactic and therapeutic treatment.

Thus, in another aspect the present invention provides a pharmaceutical or veterinary composition for prophylactic or therapeutic inhibition of a microbial or parasitic agent in a human or non-human animal patient, which comprises a dendrimer as broadly described above, in association with at least one pharmaceutically or veterinarily acceptable carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect, this invention provides the use of an effective amount of a dendrimer as broadly described above in the prophylactic or therapeutic treatment of, or in the manufacture of a medicament for prophylactic or therapeutic treatment of a human or non-human animal patient by inhibition of a microbial or parasitic agent.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, inhalation, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

The active component may also be formulated for delivery in a system designed to administer the active component intranasally or by inhalation, for example as a finely dispersed aerosol spray containing the active component.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffuisional systems in which the active component permeates at a controlled rate through a polymer. In addition, a pump-based hardware delivery system can be used, some of which are adapted for implantation.

The active component is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

The active component according to the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Figure 1:
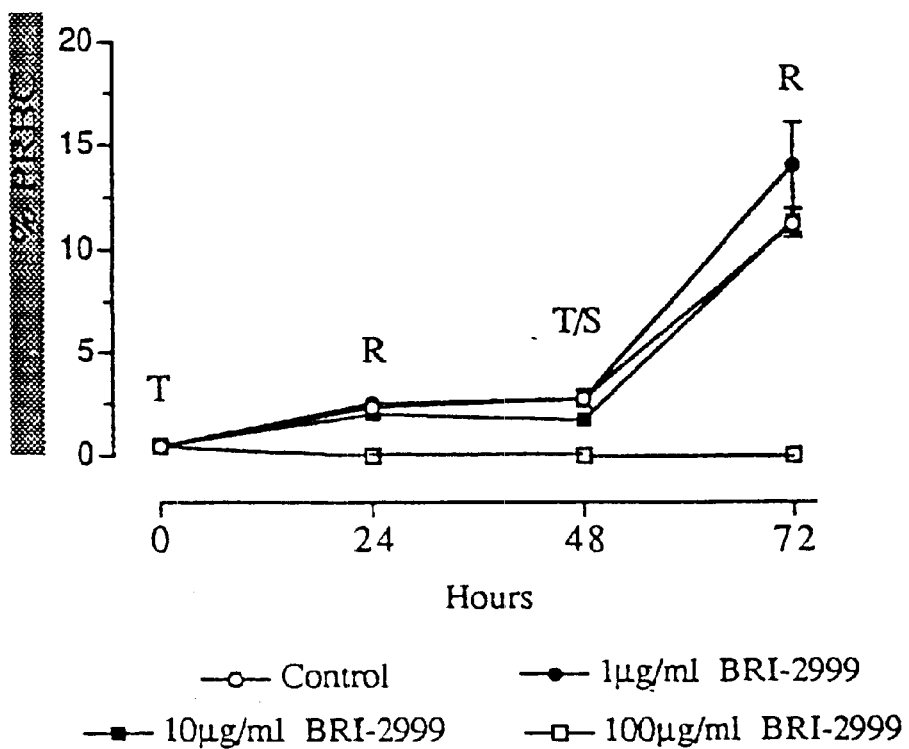
FIG. 1 shows the effect of BRI 2999 on growth of P. falciparum in human red blood cells in vitro.

Further features of the present invention will be apparent from the following Examples which are included by way of illustration, not limitation of the invention. In the following Examples, PAMAM dendrimers refer to polyamidoamine dendrimers based on an ammonia core as detailed in U.S. Pat. Nos. 4,507,466, 4,558,120, 4,568,737 and 4,587,329; PAMAM (EDA) dendrimers refer to polyamidoamine dendrimers based on an ethylene diamine core; and $BHAlys_x lys_y lys_z$ dendrimers refer to polylysine unsymmetrical dendrimers based on a benzhydrylamine core and lysine branching units as described in U.S. Pat. Nos. 4,289,872 and 4,410,688. The polyamidoamine dendrimers PAMAM 1.0, PAMAM 2.0, PAMAM 3.0, PAMAM 4.0, PAMAM 5.0 or higher generation, PAMAM 4.0 (EDA), and the polylysine dendrimers $BHAlyslys_2$, $BHAlyslys_2 lys_4$, $BHAlyslys_2 lys_4 lys_8$ and $BHAlyslys_2 lys_4 lys_8 lys_{16}$, $BHAlyslys_2 lys_4 lys_8 lys_{32}$, $BHAlyslys_2 lys_4 lys_8 lys_{16} lys_{32} lys_{64}$, or higher generations prepared as described in U.S. Pat. Nos. 4,289,872, 4,410,688, 4,507,466, 4,558,120, 4,568,737 and 4,578,239 and International Patent Publications Nos. WO 88/01178, WO 88/01179, WO 88/01180 and WO 95/24221 referred to above.

EXAMPLE 1

Reaction of Dendritic Polymers with 2-Acrylamido-2-methyl Propane Sulfonic Acid to Give Sulfonic Acid Terminated Dendrimers

A PAMAM 1.0

Solid sodium carbonate (0.13 g; 1.0 mmol) was added slowly to a stirred solution of 2-acrylamido-2-methyl propane sulfonic acid (0.41 g; 2.0 mmol) in water (3 ml). After the evolution of gas had ceased, the pH of the solution was 8.0. A solution of PAMAM 1.0 (0.12 g; 0.33 mmol) in water (1 ml) was then added to the solution followed by the addition of four drops of a 40% aq. solution of benzyl trimethylammonium hydroxide. The solution was then heated under nitrogen at 60° for three days and then concentrated. The residue was purified by gel filtration (Sephadex G10; water) and then freeze dried to give the sulfonated PAMAM 1.0 dendrimer as an off white solid (0.51 g). $^1H$ and $^{13}C$ nmr spectra showed a mixture of dialkylated and monoalkylated PAMAM 1.0 dendrimer (ca. 70:30). $^{13}C$ nmr ($D_2O$): δ 31.0, 31.1, 37.1, 37.7, 41.3, 48.6, 51.5, 53.1, 53.4, 55.6, 56.2, 61.2, 61.5, 178.3, 179.0, 179.8.

B PAMAM 2.0

PAMAM 2.0 was reacted with 2-acrylamido-2-methyl propane sulfonic acid as described above. The crude product was purified by gel filtration (Sephadex G10; water) and then freeze dried to give an off white solid. $^1H$ and $^{13}C$ nmr spectra showed a mixture of dialkylated and monoalkylated PAMAM 2.0 dendrimer (ca. 65:35). $^{13}C$ nmr ($D_2O$): δ 31.0, 31.1, 37.1, 37.7, 41.3, 48.7, 51.5, 53.4, 55.6, 56.2, 61.2, 61.5, 178.4, 179.0, 179.1, 179.6.

When the above reaction was repeated omitting the benzyltrimethylammonium hydroxide a similar result was obtained.

C PAMAM 3.0 BRI2783

PAMAM 3.0 was reacted with 2-acrylamido-2-methyl propane sulfonic acid as above except that a slight excess of sodium carbonate was used and the benzyltrimethylammonium hydroxide was omitted. $^1$H and $^{13}$C nmr spectra showed a mixture of dialkylated and monoalkylated PAMAM 3.0 dendrimer (ca. 50:50). $^{13}$C nmr (D$_2$O): δ 31.0, 31.1, 36.9, 37.4, 41.1, 48.6, 51.5, 53.4, 55.7, 56.2, 61.1, 61.5, 178.2, 178.9, 179.0, 179.8.

D PAMAM 4.0 BRI2784

PAMAM 4.0 was reacted with 2-acrylamido-2-methyl propane sulfonic acid as described for PAMAM 3.0. $^1$H and $^{13}$C nmr spectra showed a mixture of dialkylated and monoalkylated PAMAM 4.0 dendrimer (ca. 35:65). $^{13}$C nmr (D$_2$O): δ 31.0, 31.1, 36.9, 37.3, 41.1, 48.5, 51.5, 53.5, 55.7, 56.2, 61.1, 61.5, 178.1, 178.9, 179.0, 179.8.

EXAMPLE 2

Preparation of Sodium Sulfoacetamide Terminated Dendrimers

A PAMAM 1.0

A solution of 4-nitrophenyl bromoacetate (0.40 g; 1.5 mmol) in dry DMF (1 ml) was added to a stirred solution of PAMAM 1.0 (0.18 g; 0.5 mmol) in DMF (3 ml). The resulting yellow solution was stirred for 20 hours at room temperature, when a ninhydrin test was negative. The solution was concentrated (30°/0.1 mmHg) to give a yellow oil. This oil was partitioned between water and chloroform and the aqueous layer separated and washed with chloroform (2×) and finally with ethyl acetate. The aqueous solution was concentrated (35°/25 mmHg) to give the bromoacetylated PAMAM 1.0 dendrimer as a yellow oil (0.36 g;100% ). $^{13}$C nmr (D$_2$O): δ 32.8, 33.3, 43.0, 43.5, 54.4, 174.5, 176.4.

A solution of sodium sulfite (0.2 g; 1.6 mmol) in water (1 ml) was added to a solution of the bromoacetylated PAMAM 1.0 dendrimer described above (0.36 g; 0.5 mmol) in water (5 ml) and the solution left to stand at room temperature for eleven days. The yellow solution was concentrated to give a yellowish solid (0.60 g). $^{13}$C nmr (D$_2$O): δ 34.4, 43.1, 43.4, 54.0, 61.7, 171.3, 177.2.

The above reaction sequence could be carried out without isolating the bromoacetylated dendrimer by simply adding the sodium sulfite solution to the crude aqueous extract obtained from the first reaction.

B PAMAM 2.0

Method 1:

A solution of 4-nitrophenyl bromoacetate (0.18 g; 0.7 mmol) in dry DMF (1 ml) was added to a stirred solution of PAMAM 2.0 (0.10 g; 0.1 mmol) in DMF (3 ml). The resulting yellow solution was stirred for 20 hours at room temperature, when a ninhydrin test was negative. The solution was then added with swirling to water (150 ml) and the mixture extracted with chloroform (3×) and ethyl acetate. A solution of sodium sulfite (0.1 g; 0.8 mmol) in water (1 ml) was added to the crude bromoacetylated dendrimer solution and the mixture allowed to stand for three days at room temperature. The yellowish solution was then concentrated to give a yellow solid residue, which was purified by gel filtration (Sephadex LH20; water) to give the sodium sulfoacetamide terminated PAMAM 2.0 dendrimer (103 mg). $^{13}$C nmr (D$_2$O): δ 33.0, 35.7, 36.0, 37.7, 40.3, 43.0, 43.2, 53.4, 53.7, 56.0, 61.6, 171.2, 174.6, 178.5.

Method 2:

Solid succinimidyl acetylthioacetate (67 mg; 0.33 mmol) was added to a solution of PAMAM 2.0 (52 mg; 0.05 mmol) in dry DMF (2 ml) and the resulting solution stirred at room temperature for two days. The mixture was then concentrated (30°/10$^{-3}$ mmHg) to give an oily residue. The residue was partitioned between water and chloroform, and the water layer separated and concentrated to give a viscous oil (117 mg). $^1$H and $^{13}$C nmr showed the oil to be a mixture of the acylated dendrimer and N-hydroxy succinimide. Gel filtration (Sephadex G10; water) provide a pure sample of the acetylthioacetamide terminated PAMAM 2.0 dendrimer (29 mg). $^{13}$C nmr (D$_2$O): δ 34.0, 34.2, 37.3, 43.0, 43.1, 43.3, 53.5, 54.0, 56.3, 175.4, 177.2, 177.5.

A solution of the above functionalised dendrimer in 40% aqueous formic acid (7 ml) was then added to an ice cold freshly prepared solution of performic acid (1.6 mmol) in formic acid (2 ml). The mixture was stirred for one hour at 0° and then for twenty hours at room temperature. A small amount of activated charcoal was then added to decompose any excess peracid, the mixture stirred for 30 minutes then filtered and concentrated to give a viscous oil.

The crude product was dissolved in water, the pH adjusted to 9.0 with aqueous sodium bicarbonate and the material desalted by passage through a column of Sephadex G10. A white solid (20 mg;) was obtained after lyophylisation which was spectroscopically essentially the same as the material obtained by method 1. $^{13}$C nmr (D$_2$O): δ 33.0, 38.7, 42.9, 43.0, 43.1, 53.9, 54.3, 56.5, 61.6, 171.2, 176.4, 177.0.

EXAMPLE 3

Preparation of Sodium Sulfosuccinamic Acid Terminated Dendrimers

A PAMAM 1.0

Solid maleic anhydride (0.11 g; 1.1 mmol) was added to a stirred solution of PAMAM 1.0 (0.12 g; 0.33 mmol) in dry DMF (3 ml). The mixture became a little warm and brownish as the anhydride dissolved and the resulting solution was stirred overnight at room temperature. The solution was then concentrated (30°/10$^{-4}$ mmHg) to give a viscous oil. $^1$H and $^{13}$C nmr (D$_2$O) showed complete conversion of the PAMAM 1.0 to the trisamide together with some maleic acid. $^{13}$C nmr (D$_2$O): δ 33.1, 42.8, 43.1, 54.3, 135.0, 137.1, 169.1, 171.9, 173.3.

The crude trisamide was then dissolved in water (4 ml) and solid sodium sulfite (0.20 g; 1.6 mmol) added. The resulting solution was allowed to stand at room temperature for four days and then concentrated. $^1$H and $^{13}$C nmr (D$_2$O) showed a 1:1 mixture of the regioisomeric sodium sulfosuccinamic acid terminated PAMAM 1.0 dendrimers together with some sulfosuccinic acid. The crude product was purified by gel filtration (Sephadex G10; water) to afford a sample of the sodium sulfosuccinamic acid terminated PAMAM 1.0 dendrimers (107 mg). $^{13}$C nmr (D$_2$O): δ 33.3, 39.6, 40.0, 42.9, 43.1, 54.0, 67.9, 69.4, 173.8, 176.3, 177.6, 181.8.

B PAMAM 2.0

A mixture of the regioisomeric sodium sulfosuccinamic acid terminated PAMAM 2.0 dendrimers was prepared as described above. $^{13}$C nmr PAMAM 2.0 maleamic acid derivative (D$_2$O): δ 32.8, 33.0, 38.7, 42.9, 53.8, 54.3, 56.5, 135.2, 136.8, 169.2, 171.9, 173.5, 176.6. $^{13}$C nmr PAMAM 2.0 sodium sulfosuccinamic acid derivatives (D$_2$O): δ 37.0, 40.1, 41.1, 43.0, 43.2, 43.9, 53.0, 53.3, 55.5, 68.0, 69.4, 173.8, 177.6, 179.1, 179.5, 179.8, 182.3.

C PAMAM 4.0 BRI6038

Solid maleic anhydride (60 mg; 0.6 mmol) was added to a stirred solution of PAMAM 4.0 (51 mg; 0.01 mmol) in dry DMF (2 ml). The mixture initially became cloudy but soon gave a clear solution which was stirred overnight at room temperature. The solution was then concentrated (35°/10$^{-4}$ mmHg) to give a viscous oil. $^1$H and $^{13}$C nmr (D$_2$O) showed complete conversion of the PAMAM 4.0 to the polyamide together with some maleic acid. The crude polyamide was then dissolved in water (2 ml) and a solution of sodium sulfite (126 mg; 1.0 mmol) in water (2 ml) added. The resulting solution was allowed to stand at room temperature for two days and then concentrated. $^1$H and $^{13}$C nmr (D$_2$O) showed a mixture of the regioisomeric sodium sulfosuccinamic acid terminated PAMAM 4.0 dendrimers together with some sulfosuccinic acid. The crude product was purified by gel filtration (Sephadex LH20; water) to afford a sample of PAMAM 4.0 terminated with 24 regioisomeric sulfosuccinamic acid groups (90 mg). $^1$H nmr (D$_2$O): δ 2.4–2.6; 2.7–3.1; 3.2–3.4; 3.9–4.0. $^{13}$C nmr (D$_2$O): δ 36.2; 39.8; 40.5; 43.0; 43.2; 53.5; 55.8; 68.1; 69.5; 173.8; 177.4; 177.6; 178.7; 182.3.

EXAMPLE 4

Preparation of Sodium N-(2-Sulfoethyl)succinamide Terminated Dendrimers a Preparation of Tetrabutylammonium N-(2-Sulfoethyl) succinamic Acid Solid succinic anhydride (0.5 g; 5.0 mmol) was added to a stirred solution of tetrabutylammonium 2-aminoethylsulfonic acid (1.83 g; 5.0 mmol) in dry dichloromethane (30 ml). The succinic anhydride slowly dissolved and the resulting cloudy solution was stirred overnight at room temperature. The mixture was filtered and the filtrate concentrated to give a viscous oil (2.41 g). $^{13}$C nmr showed complete conversion to the desired monoamide together with a small amount of succinic acid. Repeated precipitation of the product by dropwise addition of a dichloromethane solution to a large excess of diethyl ether gave tetrabutylammonium N-(2-sulfoethyl)succinamic acid as a white solid (1.762 g; 76%), mp 125–127° C. $^1$H nmr (CDCl$_3$): δ 0.86 (t, 12H, 4×CH$_3$), 1.28 (m, 8H, 4×CH$_2$), 1.50 (m, 8H, 4×CH$_2$), 2.33 (m, 2H, CH$_2$COOH), 2.44 (m, 2H, CH$_2$CONH), 2.76 (m, 2H, CH$_2$NHCO), 3.12 (m, 8H, 4×CH$_2$N), 3.50 (m, 2H, CH$_2$SO$_3$), 7.53 (br t, 1H, NH). $^{13}$C nmr (CDCl$_3$): δ 13.5 ,19.5, 23.8, 30.1, 30.9, 35.6, 50.0, 58.5, 172.0, 174.1.

b Preparation of Tetrabutylammonium 4-Nitrophenyl N-(2-Sulfoethyl)succinamate

A solution of dicyclohexylcarbodiimide (45 mg; 0.22 mmol) in dry dichloromethane (1 ml) was added to a stirred solution of tetrabutylammonium N-(2-sulfoethyl) succinamic acid (94 mg; 0.20 mmol) in dichloromethane (2 ml), and the mixture stirred overnight at room temperature. The resulting suspension was filtered and the filtrate concentrated to give the crude active ester, which was used without further purification.

A Preparation of Sodium N-(2-Sulfoethyl) succinamide Terminated PAMAM Dendrimers

PAMAM 4.0 BRI2786

A solution of the crude tetrabutylammonium 4-nitrophenyl N-(2-sulfoethyl)succinamate (0.30 mmol) in dry DMF (1 ml) was added to a stirred solution of PAMAM 4.0 (51.5 mg; 0.01 mmol) dissolved in 50% aqueous DMF (3 ml) and the resulting yellow solution stirred overnight at room temperature. The mixture was then concentrated (35°/10$^{-5}$ mmHg) and the yellow residue partitioned between water and chloroform. The water layer was separated, washed with chloroform (2×) and ethyl acetate, and then concentrated to give a yellow oil (134 mg). The crude product was converted to the sodium salt by passage through a column of Amberlite IR 120(Na) to yield 85 mg of material. This material was further purified by gel filtration (Sephadex LH20; water) to give the sodium N-(2-sulfoethyl) succinamide terminated PAMAM 4.0 dendrimer (45 mg). $^{13}$C nmr (D$_2$O): δ 33.2, 33.6, 35.5, 39.0, 39.5, 42.8, 43.2, 53.8, 54.1, 54.4, 56.6, 176.5, 176.9, 177.2, 178.9, 179.4.

The corresponding PAMAM 1.0 and PAMAM 3.0 (BRI2785) dendrimers terminated with sodium N-(2-sulfoethyl)succinamide groups were similarly prepared. $^{13}$C nmr PAMAM 3.0 derivative (D$_2$O): δ 33.4, 35.5, 39.0, 39.5, 42.9, 43.2, 53.8, 54.1, 54.3, 56.5, 176.4, 176.9, 177.4, 178.9, 179.4. $^{13}$C nmr PAMAM 1.0 derivative (D$_2$O): δ 34.9, 35.5, 39.5, 42.9, 43.1, 53.7, 54.1, 179.0, 179.1, 179.3.

B Preparation of Sodium N-(2-Sulfoethyl) succinamide Terminated Polylysine Dendrimers BHAlyslys$_2$lys$_4$lys$_8$lys$_{16}$ BRI2789

Trifluoroacetic acid (1 ml) was added to a suspension of BHAlyslys$_2$lys$_4$lys$_8$DBL$_{16}$ (36.5 mg; 5.0 μmmol) in dry dichloromethane (1 ml) and the resulting solution stirred at room temperature under nitrogen for two hours and then concentrated. The residue was dissolved in dry DMSO (2 ml) and the pH adjusted to 8.5 with triethylamine. A solution of the crude tetrabutylammonium 4-nitrophenyl N-(2-sulfoethyl)succinamate (ca. 0.2 mmol) in DMSO (1 ml) was then added dropwise and the mixture stirred overnight at room temperature. The yellow solution was then concentrated (50°/10$^{-5}$ mmHg) and the yellow residue partitioned between water and chloroform. The aqueous layer was separated, washed with chloroform (3×) and ethyl acetate, and then concentrated to give an oil (99 mg). The crude product was converted to the sodium salt by passage through a column of Amberlite IR 120(Na) to yield 81 mg of material. This material was further purified by gel filtration (Sephadex LH20; water) to give the sodium N-(2-sulfoethyl) succinamide terminated BHAlyslys$_2$lys$_4$lys$_8$lys$_{16}$ dendrimer (39 mg). $^{13}$C nmr (D$_2$O): δ 27.0, 32.3, 35.2, 35.3, 35.6, 35.7, 39.5, 43.5, 54.1, 58.5, 131.5, 132.0, 133.3, 145.1, 177.8, 178.0, 178.4, 178.8, 178.9, 179.2, 179.7, 179.8.

The corresponding BHAlyslys$_2$, BHAlyslys$_2$lys$_4$ (BRI2787) and BHAlyslys$_2$lys$_4$lys$_8$ (BRI2788) terminated with sodium N-(2-sulfoethyl)succinamide groups were similarly prepared. $^{13}$C nmr BHAlyslys$_2$lys$_4$lys$_8$ derivative (D$_2$O): δ 26.9, 32.3, 35.1, 35.3, 35.6, 35.7, 39.5, 43.5, 54.1, 58.5, 131.6, 131.9, 132.2, 132.3, 133.2, 133.3, 145.0, 145.2, 177.2, 177.8, 177.9, 178.0, 178.2, 178.3, 178.6, 178.7, 178.8, 178.9, 179.2, 179.3, 179.7, 179.8. $^{13}$C nmr BHAlyslys$_2$lys$_4$ derivative (D$_2$O): δ 26.9, 32.3, 35.1, 35.4, 35.7, 35.8, 39.5, 43.5, 54.1, 58.5, 61.8, 131.7, 132.0, 132.2, 132.3, 133.2, 133.3, 145.0, 145.1, 177.3, 178.0, 178.3, 178.4, 178.7, 178.9, 179.0, 179.3, 179.7, 179.8. $^{13}$C nmr BHAlyslys$_2$ derivative (D$_2$O): δ 26.9, 27.1, 32.2, 32.3, 34.7, 34.8, 35.1, 35.3, 35.6, 35.7, 39.5, 43.4, 54.1, 58.6, 61.8, 131.7, 131.9, 132.2, 132.3, 133.3, 144.9, 145.0, 177.7, 178.4, 178.8, 179.0, 179.3, 180.0.

EXAMPLE 5

Preparation of Sodium 4-Sulfophenylthiourea Terminated Dendrimers

A PAMAM 4.0 BRI2791

Solid sodium 4-sulfophenylisothiocyanate monohydrate (500 mg; 1.96 mmol) was added to a solution of PAMAM 4.0 (300 mg; 0.0582 mmol) in water (10 ml) and the resulting solution heated under nitrogen at 53° for two hours and then cooled. The solution was concentrated and the yellow solid residue purified by gel filtration (Sephadex LH20; water). The pure fractions were combined and freeze dried to give the sodium 4-sulfophenylthiourea terminated PAMAM 4.0 dendrimer as a fluffy white solid (370 mg). $^1$H nmr (D$_2$O): δ 2.28; 2.52; 2.69; 3.15; 3.27; 3.60; 7.32 (d, J=9 Hz); 7.72 (d, J=9 Hz). $^{13}$C nmr (D$_2$O): δ 36.9; 41.1; 43.1; 48.3; 53.6; 55.8; 129.0; 131.1; 144.4; 178.5; 179.1; 184.4.

The corresponding PAMAM 1.0, PAMAM 2.0 (BRI2790), PAMAM 3.0, and PAMAM 5.0 (BRI2991) dendrimers terminated with 3, 6, 12, and 48 sodium 4-sulfophenylthiourea groups respectively were similarly prepared.

B PAMAM 4.0 (EDA) BRI6045

Solid sodium 4-sulfophenylisothiocyanate monohydrate (130 mg; 0.5 mmol) was added to a solution of PAMAM 4.0 (EDA) (69 mg; 0.01 mmol) in water (4 ml) and the resulting solution heated under nitrogen at 53° for two hours and then cooled. The solution was concentrated and the solid residue purified by gel filtration (Sephadex LH20; water). The pure fractions were combined and freeze dried to give PAMAM 4.0 terminated with 32 sodium 4-sulfophenylthiourea groups as a fluffy white solid (136 mg). $^1$H nmr (D$_2$O): δ 2.30; 2.50; 2.70; 3.18; 3.62; 7.35 (d, J=9 Hz); 7.72 (d, J=9 Hz). $^{13}$C nmr (D$_2$O): δ 36.8; 41.0; 43.1; 48.4; 53.6; 55.7; 128.9; 131.0; 144.3; 178.5; 179.0; 184.5.

C BHAlyslys$_2$lys$_4$lys$_8$lys$_{16}$ BRI2792

Trifluoroacetic acid (4 ml) was added to a suspension of BHAlyslys$_2$lys$_4$lys$_8$DBL$_{16}$ (0.73 g; 0.1 mmol) in dry dichloromethane (4 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401(OH) and the filtrate concentrated to give BHAlyslys$_2$lys$_4$lys$_8$lys$_{16}$ as a viscous oil (0.49 g). The oil was redissolved in water (5 ml) and N,N-dimethyl-N-allylamine buffer (pH 9.5; 3 ml) added. Solid sodium 4-sulfophenylisothiocyanate monohydrate (1.30 g; 5.1 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120(Na) and freeze dried to give the sodium 4-sulfophenylthiourea terminated BHAlyslys$_2$lys$_4$lys$_8$lys$_{16}$ dendrimer as a fluffy white solid (374 mg). $^1$H nmr (D$_2$O): δ 1.40; 1.72; 3.08; 3.42; 4.24; 4.60; 7.30; 7.40 (d, J=9 Hz); 7.78 (d, J=9 Hz). $^{13}$C nmr (D$_2$O): δ 27.3; 32.5; 35.9; 43.7; 48.9; 58.6; 63.3; 128.8; 131.0; 143.7; 144.7; 145.1; 177.7; 178.1; 183.8; 185.2.

The corresponding BHAlyslys$_2$lys$_4$lys$_8$, BHAlyslys$_2$lys$_4$lys$_8$lys$_{16}$lys$_{32}$ (BRI2992), and BHAlyslys$_2$lys$_4$lys$_8$lys$_{16}$lys$_{32}$lys$_{64}$ (DRI2993) dendrimers terminated with 16, 64, and 128 sodium 4-sulfophenylthiourea groups respectively were similarly prepared.

EXAMPLE 6

Preparation of Sodium 3,6-Disulfonapthylthiourea Terminated Dendrimers

A PAMAM 4.0 BRI2923

Solid sodium 3,6-disulfonapthylisothiocyanate (160 mg; 0.41 mmol) was added to a solution of PAMAM 4.0 (51 mg; 0.00 mmol) in water (3 ml) and the resulting solution heated under nitrogen at 53° for two hours and then cooled. The solution was concentrated and the brown solid residue purified by gel filtration (Sephadex LH20; water). The pure fractions were combined and concentrated to give the sodium 3,6-disulfonapthylthiourea terminated PAMAM 4.0 dendrimer as a brownish solid (73 mg). $^1$H nmr (D$_2$O): δ 2.30; 2.60; 2.74; 3.20; 3.57; 7.75; 7.86; 8.28. $^{13}$C nmr (D$_2$O): δ 35.0; 39.9; 43.1; 48.1; 53.8; 56.1; 128.4; 128.6; 129.3; 131.0; 131.3; 136.0; 136.8; 138.2; 145.5; 146.0; 177.2; 177.8; 185.5.

The corresponding PAMAM 2.0 dendrimer terminated with sodium 3,6-disulfonapthylthiourea groups was similarly prepared.

B PAMAM 4.0 (EDA) BRI6046

Solid sodium 3,6-disulfonapthylisothiocyanate (220 mg; 0.57 mmol) was added to a solution of PAMAM 4.0 (EDA) (74 mg; 0.01 mmol) in water (4 ml) and the resulting solution heated under nitrogen at 53° for two hours and then cooled. The solution was concentrated and the brownish solid residue purified by gel filtration (Sephadex LH20; water). The pure fractions were combined and concentrated to give PAMAM 4.0 terminated with 32 sodium 3,6-disulfonapthylthiourea groups as a tan solid (148 mg). $^1$H nmr (D$_2$O): δ 2.30; 2.80; 3.20; 3.54; 7.74; 7.85; 8.25. $^{13}$C nmr (D$_2$O): δ 36.0; 40.8; 43.1; 48.3; 53.6; 55.9; 128.5; 129.4; 131.0; 131.3; 136.0; 136.8; 138.3; 145.5; 146.0; 178.2; 185.6.

C BHAlyslys$_2$lys$_4$lys$_8$lys$_{16}$ BRI2999

Trifluoroacetic acid (2 ml) was added to a suspension of BHAlyslys$_2$lys$_4$lys$_8$DBL$_{16}$ (73 mg; 0.01 mmol) in dry dichloromethane (2 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401(OH) and the filtrate concentrated to give BHAlslys$_2$lys$_4$lys$_8$lys$_{16}$ as a viscous oil. The oil was redissolved in water (5 ml) and N,N-dimethyl-N-allylamine buffer (pH 9.5; 3 ml) added. Solid sodium 3,6-disulfonapthylisothiocyanate (234 mg; 0.60 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120 (Na) and freeze dried to give BHAlyslys$_2$lys$_4$lys$_8$lys$_{16}$ terminated with 32 sodium 3,6-disulfonapthylthiourea groups as a fluffy off-white solid (119 mg). $^1$H nmr (D$_2$O): δ 1.0–2.0; 3.18; 3.43; 4.31; 7.22; 7.80; 7.89; 8.25. $^{13}$C nmr (D$_2$O): δ 27.2; 32.4; 35.3; 43.7; 49.0; 58.5; 63.6; 128.4; 129.1; 131.4; 136.1; 136.6; 138.6; 139.0; 145.1; 145.6; 178.4; 184.8; 186.7.

EXAMPLE 7

Preparation of Sodium 4-Sulfonapthylthiourea Terminated Dendrimers

PAMAM 4.0 BRI2997

Solid sodium 4-sulfonapthylisothiocyanate (180 mg; 0.5 mmol) was added to a solution of PAMAM 4.0 (51 mg; 0.01 mmol) in water (5 ml) and the mixture heated under nitrogen at 53° for two hours and then cooled. The water was distilled under reduced pressure from the resulting suspension and the off white solid residue purified by gel filtration (Sephadex LH20; water). The pure fractions were combined and freeze dried to give the sodium 4-sulfonapthylthiourea terminated PAMAM 4.0 dendrimer as a fluffy white solid (60 mg). $^1$H nmr (D$_2$O): δ 2.20; 2.60; 3.14; 3.48; 7.23; 7.47; 7.56; 7.77; 7.93 (d, J=6 Hz); 8.56 (d, J=6 Hz). $^{13}$C nmr (D$_2$O): δ 35.8; 40.5; 43.1; 48.4; 53.6; 55.9; 127.6; 128.6; 130.3; 131.9; 132.5; 133.5; 134.7; 140.5; 142.7; 177.8; 178.0; 185.4.

EXAMPLE 8

Preparation of Sodium 3,5-Disulfophenylthiourea Terminated Dendrimers

PAMAM 4.0 BRI6039

Solid sodium 3,5-disulfophenylisothiocyanate (110 mg; 0.32 mmol) was added to a solution of PAMAM 4.0 (63 mg; 0.012 mmol) in water (3 ml) and the resulting solution heated under nitrogen at 53° for two hours and then cooled. The solution was concentrated and the brownish solid residue purified by gel filtration (Sephadex G25; water). The pure fractions were combined and concentrated to give PAMAM 4.0 terminated with 24 sodium 3,5-disulfophenylthiourea groups as an off-white solid (110 mg). $^1$H nmr ($D_2O$): δ 2.53; 3.08; 3.36; 3.66; 7.90; 7.95. $^{13}$C nmr ($D_2O$): δ 34.8; 41.0; 43.1; 48.0; 53.7; 56.2; 124.1; 128.6; 143.5; 148.8; 177.6; 185.0.

EXAMPLE 9

Preparation of Sodium 3,6,8-Trisulfonaphthylthiourea Terminated Dendrimers

PAMAM 4.0 BRI2998

Solid sodium 3,6,8-trisulfonaphthylisothiocyanate (250 mg; 0.5 mmol) was added to a solution of PAMAM 4.0 (51 mg; 0.01 mmol) and N,N-dimethyl-N-allylamine buffer (pH 9.5; 1 ml) in water (2 ml) and the mixture heated under nitrogen at 53° for two hours and then cooled. The mixture was concentrated under reduced pressure to give an orange solid. The residual solid was dissolved in water (2 ml) and passed through a short column of Amberlite IR-120(Na). The filtrate was then concentrated and the residue purified by gel filtration (Sephadex LH20; water). The pure fractions were combined and freeze dried to give the sodium 3,6,8-trisulfonaphthylthiourea terminated PAMAM 4.0 dendrimer as an off-white solid (102 mg). $^1$H nmr ($D_2O$): δ 2.65; 3.02; 3.30; 3.66; 8.05; 8.42; 8.59; 8.67. $^{13}$C nmr ($D_2O$): δ 33.2; 38.7; 43.2; 43.7; 47.8; 54.0; 54.3; 56.7; 131.0; 131.3; 131.9; 135.9; 138.0; 139.6; 143.8; 144.1; 145.6; 176.2; 176.5; 186.0.

The corresponding sodium 3,6,8-trisulfonaphthylthiourea terminated dendrimer BHAlys.lys$_2$lys$_4$lys$_8$lys$_{16}$ BRI 7011 was prepared similarly.

EXAMPLE 10

Preparation of Sodium 4-(Sulfomethyl)benzamide Terminated Dendrimers

PAMAM 4.0 BRI6040

Solid 4-nitrophenyl 4-(chloromethyl)benzoate (200 mg; 0.68 mmol) was added to a stirred solution of PAMAM 4.0 (70 mg; 0.014 mmol) in dry DMSO (4 ml) and the resulting yellow solution stirred at room temperature for two hours. The solution was then concentrated ($10^{-4}$ mmHg; 40°) and the residue extracted with a mixture of water and dichloromethane (1:1). The remaining solid material was dissolved in DMSO (5 ml) and a solution of sodium sulfite (130 mg; 1 mmol) in water (3 ml) added. The slightly cloudy mixture that resulted was left to stand for four days, after which time the addition of more water (2 ml) resulted in the formation of a clear homogeneous yellow solution. The solution was then concentrated, first at 25 mmHg and 40° then at $10^{-4}$ mmHg and 50° to give the crude product. The crude product was purified by gel filtration (Sephadex G25; water) to give PAMAM 4.0 terminated with 24 sodium 4-(sulfomethyl) benzamide groups (24 mg). $^1$H nmr ($D_2O$): δ 2.25; 2.66; 3.08; 3.20; 3.33; 3.38; 4.01; 7.40 (br d); 7.62 (br d). $^{13}$C nmr ($D_2O$): δ 36.7; 40.9; 43.0; 43.6; 53.5; 55.5; 61.0; 131.6; 135.0; 137.2; 140.4; 174.5; 178.6; 179.2.

EXAMPLE 11

Preparation of 4-Sulfobenzamide Terminated Dendrimers

PAMAM 4.0 (EDA) BRI6116

Solid potassium N-hydroxysuccinimidyl 4-sulfobenzoate (100 mg; 0.3 mmol) was added to a solution of PAMAM 4.0 (EDA) (35 mg; 0.005 mmol) in 0.1M pH 8.5 borate buffer (5 ml) and the solution stirred at room temperature for two hours. The resulting milky solution at this stage had a pH of 4.5. 1M Sodium carbonate solution (1 ml) was then added to give a clear solution which was concentrated to give the crude product as a white solid. The crude product was purified by gel filtration (Sephadex G25; water) to give PAMAM 4.0 (EDA) terminated with 32 sodium 4-sulfobenzamide groups (47 mg). $^1$H nmr ($D_2O$): δ 2.25; 2.42; 2.63; 3.05; 3.18; 3.31; 3.38; 7.72 (d, J=8 Hz); 7.78 (d, J=8 Hz). $^{13}$C nmr ($D_2O$): δ 36.0; 40.4; 43.0; 43.7; 53.7; 55.8; 130.2; 132.2; 140.4; 150.1; 173.6; 178.0; 178.5.

EXAMPLE 12

Preparation of Sodium N-(4-Sulfophenyl) propanamide Terminated Dendrimers

PAMAM 4.0 (EDA) BRI6117

Solid sodium N-(4-sulfophenyl)acrylamide (250 mg; 1 mmol) and solid sodium carbonate (106 mg; 1 mmol) were added successively to a stirred solution of PAMAM 4.0 (EDA) (78 mg; 0.011 mmol) in water (4 ml). The resulting solution was stirred under nitrogen for four days and then freeze dried to give a fluffy white solid. The crude product was purified by gel filtration (Sephadex LH20; water to give PAMAM 4.0 (EDA) terminated with 64 sodium N-(4-sulfophenyl)propanamide groups (206 mg). $^{13}$C nmr showed a faint trace of what was taken to be mono alkylated terminal amino groups. $^1$H nmr ($D_2O$): δ 2.10; 2.48; 2.58; 2.79; 3.20; 7.42 (d, J=7 Hz); 7.65 (d, J=7 Hz). $^{13}$C nmr ($D_2O$): δ 36.5; 37.9; 41.1; 53.4; 55.6; 124.8; 130.9; 143.0; 144.2; 177.4; 178.5.

EXAMPLE 13

Preparation of Sodium 4-Sulfophenylurea Terminated Dendrimers

PAMAM 4.0 (EDA) BRI6115

A solution of sodium sulfanilic acid (195 mg; 1 mmol) in dry DMSO (3 ml) was added dropwise to a solution of N,N'-disuccinimidyl carbonate (530 mg; 2 mmol) in dry DMSO (4 ml) and the resulting brownish solution stirred at room temperature for 20 hours. A solution of PAMAM 4.0 (EDA) (75 mg; 0.011 mmol) in dry DMSO (1 ml) added and the solution stirred for a further 18 hours. The solution was then concentrated under high vacuum ($10^{-5}$ mmHg; 35°) to give a yellowish semi-solid. The crude product was dissolved in DMSO (4 ml) and the solution added to 200 ml of well stirred ethyl acetate. The precipitated white solid was collected by filtration and washed with ethyl acetate (2×) and ether (2×), then dried to give a white powder (275 mg). This material was further purified by gel filtration (Sephadex LH20; water) to give PAMAM 4.0 (EDA) terminated with 32 sodium 4-sulfophenylurea groups (106 mg). $^1$H nmr (D$_2$O): δ 2.31; 2.55; 2.75; 3.19; 7.32 (d, J=9 Hz); 7.63 (d, J=9 Hz). $^{13}$C nmr (D$_2$O): δ 36.3; 40.7; 43.3; 43.8; 53.7; 55.7; 123.3; 130.9; 140.9; 146.0; 161.4; 178.2; 178.6.

EXAMPLE 14

Preparation of N,N,N-Trimethylglycinamide Chloride Terminated Dendrimers

BHAlyslys$_2$lys$_4$lys$_8$lys$_{16}$ BRI2922

Trifluoroacetic acid (4 ml) was added to a suspension of BHAlyslys$_2$lys$_4$lys$_8$DBL$_{16}$ (220 mg; 30 μmol) in dry dichloromethane (2 ml) and the resulting solution stirred at room temperature under nitrogen for two hours and then concentrated. The residue was dissolved in dry DMSO (5 ml) and the pH adjusted to 8.5 with triethylamine. Solid 4-nitrophenyl N,N,N-trimethylglycinate chloride (0.50 g; 1.8 mmol) was then added and the mixture stirred overnight at room temperature. The cloudy solution was then concentrated (50°/10$^{-5}$ mmHg) and the residue partitioned between water and dichloromethane. The aqueous layer was separated, washed with dichloromethane (3×) and ethyl acetate, and then concentrated to give an oil (1.128 g). The crude product was purified by gel filtration (Sephadex LH20; water) to give the N,N,N-trimethylglycinamide terminated BHAlyslys$_2$lys$_4$lys$_8$lys$_{16}$ dendrimer (116 mg). $^{13}$C nmr (D$_2$O): δ 25.5, 30.5, 30.8, 33.4, 42.1, 56.5, 57.1, 67.5, 68.1, 166.7, 167.0, 167.1, 176.0, 176.2.

EXAMPLE 15

Preparation of 4-Trimethylammoniumbenzamide Terminated Dendrimers

PAMAM 4.0 BRI6043

1,1'-Carbonyldiimidazole (85 mg; 0.52 mmol) was added to a solution of 4-trimethylammoniumbenzoic acid iodide (154 mg; 0.5 mmol) in dry DMF (4 ml) and the mixture stirred at room temperature under argon for two hours. During this time a white solid separated from the solution. A solution of PAMAM 4.0 (58 mg; 0.01 1 mmol) in dry DMF (2 ml) was then added and the mixture stirred overnight at room temperature. After this time most of the precipitate had dissolved and a ninhydrin test of the solution was negative. The mixture was concentrated (10$^{-4}$ mmHg; 30°) to give a white solid residue. The crude product was purified by gel filtration (Sephadex LH20; 10% AcOH) to give PAMAM 4.0 terminated with 24 4-trimethylammoniumbenzamide groups as the acetic acid salt (89 mg). $^1$H nmr (D$_2$O): δ 1.96; 2.65–2.85; 3.25–3.55; 3.64; 7.92. $^{13}$C nmr (D$_2$O): δ 25.8; 33.1; 33.5; 38.7; 43.1; 43.5; 53.5; 54.1; 56.4; 61.2; 124.8; 133.6; 139.9; 153.2; 173.2; 176.3; 176.8; 182.6.

The corresponding PAMAM 2.0 dendrimer terminated with 6 4-trimethylammonium benzamide groups was similarly prepared.

EXAMPLE 16

Preparation of 4-(Trimethylammoniummethyl) benzamide Terminated Dendrimers

PAMAM 4.0 BRI6044

Solid 4-nitrophenyl 4-(chloromethyl)benzoate (150 mg; 0.5 mmol) was added to a stirred solution of PAMAM 4.0 (52 mg; 0.01 mmol) in dry DMSO (3 ml). The resulting yellow solution was stirred at room temperature for 20 hours, when a ninhydrin test was negative (pH ca.8.5). The solution was then concentrated (10$^{-5}$ mmHg; 40°) and the residue shaken with a mixture of water and dichloromethane (1:1). The insoluble gel-like material was collected by filtration, washed with water (2×) and dichloromethane (2×), and then air dried. The crude 4-(chloromethyl)-benzamide terminated dendrimer was dissolved in 25% aq. trimethylamine (20 ml) and the yellow solution left to stand overnight. The solution was then concentrated, the residue dissolved in water (5 ml) and the solution passed through a column of Amberlite IRA-401 (OH). The colourless filtrate was concentrated to give a viscous oil which was purified by gel filtration (Sephadex G10; 10% AcOH) to give PAMAM 4.0 terminated with 24 4-(trimethylammoniummethyl) benzamide groups (90 mg). $^1$H nmr (D$_2$O): δ 1.88; 2.65–2.80; 2.98; 3.10–3.60; 7.52 (br d, J=9 Hz); 7.72 (br d, J=9 Hz). $^{13}$C nmr (D$_2$O): δ 26.6; 33.4; 38.8; 43.2; 43.5; 53.6; 53.6; 54.1; 56.8; 62.8; 73.0; 132.1; 135.3; 137.5; 140.0; 176.4; 176.9; 183.6.

EXAMPLE 17

Preparation of N-(2-Acetoxyethyl)-N,N-(dimethylammonium)methyl-carboxamide Terminated Dendrimers

PAMAM 4.0

Solid 1,1'-carbonyldiimidazole (85 mg; 0.52 mmol) was added to a solution of N-(2-acetoxyethyl)-N-(carboxymethyl)-N,N-dimethylammonium bromide (135 mg; 0.5 mmol) in dry DMF (3 ml) and the resulting solution stirred under nitrogen for two 10 hours. A solution of PAMAM 4.0 (60 mg; 0.012 mmol) in DMF (2 ml) was then added, which caused the immediate formation of a flocculant precipitate which slowly redissolved. The mixture was stirred for two days and then concentrated (10$^{-4}$ mmHg; 40°) to give a viscous oil. The crude product was purified by gel filtration (Sephadex G10; 10% AcOH) to give PAMAM 4.0 terminated with 24 N-(2-Acetoxyethyl)-N,N-(dimethylammonium)methylcarboxamide groups (64 mg). $^1$H nmr (D$_2$O): δ 1.93; 2.05; 2.70; 3.10–3.60; 3.28; 3.93 (m); 4.14; 4.48 (m). $^{13}$C nmr (D$_2$O): δ 24.6; 26.2; 33.2; 38.7; 42.8; 42.9; 53.9; 57.4; 62.6; 67.3; 67.5; 168.9; 176.4; 176.8; 177.3; 183.2.

EXAMPLE 18

Preparation of Guanidino Terminated Dendrimers

PAMAM 4.0 BRI6042

A solution of PAMAM 4.0 (63 mg; 0.012 mmol) and methylthiopseudourea sulfate (170 mg; 0.61 mmol) in water (5 ml) (pH 10.5) was heated under nitrogen at 80° for two hours. The solution was then concentrated and the residue purified by gel filtration (Sephadex G10; 10% AcOH) to give PAMAM 4.0 terminated with 24 guanidino groups as the acetate salt (107 mg). $^1$H nmr (D$_2$O): δ 2.00; 2.80 (br t); 3.09 (br t); 3.32; 3.45 (br t); 3.60 (br t). $^{13}$C nmr (D$_2$O): δ 25.2; 33.2; 33.4; 38.7; 41.2; 42.6; 43.4; 44.7; 53.5; 54.0; 56.3; 176.5; 176.7; 176.9; 181.6.

The corresponding PAMAM 2.0 dendrimer terminated with 6 guanidino groups was similarly prepared.

EXAMPLE 19

Preparation of 4-([1,4,8,11-Tetraazacyclotetradecane]methyl)benzamide Terminated Dendrimers

PAMAM 4.0 BRI6041

A solution of 1-(4-carboxyphenyl)methyl-1,4,8,11-tetraazacyclotetradecane tetra hydrochloride (120 mg; 0.25 mmol), N-hydroxysuccinimide (60 mg; 0.52 mmol) and 1-(3-dimethylaminopropyl)-3-ethylcarbodiimide hydrochloride (250 mg; 1.3 mmol) in pH 7 phosphate buffer (10 ml) was allowed to stand a room temperature for one hour and then a solution of PAMAM 4.0 (32 mg; 0.006 mmol) in pH 7 phosphate buffer (10 ml) added. The mixture was allowed to stand for two days and then concentrated. The residue was purified by gel filtration (Sephadex LH20; 10% AcOH) to give PAMAM 4.0 terminated with ca. 12 4-([1,4,8,11-tetraazacyclotetradecane]methyl)-benzamide groups as determined by $^1$H and $^{13}$C nmr (80 mg). The product was then dissolved in water and passed through a column of Amberlite IRA-401 (Cl) resin and then concentrated. The residue was dissolved in water (1 ml), concentrated HCl (1 ml) added, and the solution diluted with ethanol (30 ml) to precipitate a white solid. The solid was collected by filtration (68 mg). Once again $^1$H and $^{13}$C nmr showed ca. 50% functionalisation of the terminal amino groups. $^1$H nmr (D$_2$O): δ 2.17; 2.36; 2.50; 2.78; 2.85; 3.25; 3.40; 3.50; 3.60; 3.62; 4.49; 7.63 (br d); 7.78 (br d). $^{13}$C nmr (D$_2$O): δ 22.7; 23.1; 33.2; 38.8; 39.9; 40.2; 40.3; 41.0; 41.2; 42.0; 42.9; 43.2; 43.6; 45.5; 46.1; 49.1; 52.2; 53.9; 54.3; 56.6; 62.7; 132.5; 135.7; 137.1; 139.7; 174.3; 176.2; 176.3; 176.7; 177.0; 178.2; 178.5.

EXAMPLE 20

Preparation of 4-Carboxy-3-hydroxybenzylamine Terminated Dendrimers

PAMAM 4.0 (EDA) BRI6119

Sodium cyanoborohydride (32 mg; 0.5 mmol) was added to a mixture of PAMAM 4.0 (EDA) (69 mg; 0.01 mmol), 4-formyl-2-hydroxybenzoic acid (83 mg; 0.5 mmol), and sodium hydrogen carbonate (42 mg; 0.5 mmol) in water (4 ml). The inhomogeneous orange mixture was stirred for four hours at room temperature, during which time it became homogeneous. The orange solution was then concentrated and the residue purified by gel filtration (Sephadex LH20; water) to give PAMAM 4.0 (EDA) terminated with ca. 32 4-carboxy-3-hydroxybenzylamine groups (91 mg). $^1$H and $^{13}$C nmr (D$_2$O) shows mostly mono alkylation but with some signs of dialkylation of the terminal amino groups, both spectra show broad peaks. $^{13}$C nmr (D$_2$O): δ 37.0; 41.1; 50.9; 53.4; 55.5; 55.8; 61.5; 120.9; 122.2; 122.4; 132.3; 132.7; 135.0; 135.8; 163.5; 163.7; 169.0; 178.6; 179.3. $^1$H nmr (D$_2$O): δ 2.20; 2.35; 2.60; 3.15; 3.30; 3.55; 4.25; 6.68; 7.12; 7.55.

EXAMPLE 21

Preparation of 4-Carboxyphenylamide Terminated dendrimers

PAMAM 4.0 (EDA)

Solid 4-carboxyphenylisothiocyanate (86 mg; 0.48 mmol) was added to a solution of PAMAM 4.0 (EDA) (69 mg; 0.01 mmol) in water (20 ml). The pH of the resulting cloudy solution was adjusted to 9 with saturated NaHCO$_3$ solution and left to stir at room temperature for 24 hours. The reaction mixture was then filtered and the filtrate concentrated to give a white solid residue, which was purified by gel filtration (Sephadex LH20; water) and then freeze dried to give the product as a white fluffy solid (68 mg).

EXAMPLE 22

Preparation of 3,5-Dicarboxyphenylamide Terminated Dendrimers

PAMAM 4.0 (EDA)

Solid 3,5-dicarboxyphenylisothiocyanate (112 mg; 0.5 mmol) was added to a solution of PAMAM 4.0 (EDA) (70 mg; 0.01 mmol) in water (5 ml). The pH of the resulting cloudy solution was adjusted to 10 with 1M Na$_2$CO$_3$ solution and heated under nitrogen at 53° for 2 hours. The reaction mixture was then filtered and the filtrate concentrated to give a brownish solid residue, which was purified by gel filtration (Sephadex LH20; water) and then freeze dried to give the product as a pale brown solid (112 mg).

EXAMPLE 23

Preparation of Sodium 4-Phosphonooxyphenylthiourea Terminated Dendrimers

PAMAM 4.0 (EDA)

Solid sodium 4-phosphonooxyphenylisothiocyanate (251 mg) was added to a solution of PAMAM 4.0 (EDA) (69 mg; 0.01 mmol) in water (20 ml). The resulting solution (pH 9) was stirred for 24 hours at room temperature under nitrogen. The reaction mixture was then concentrated to give a white solid residue, which was purified by gel filtration (Sephadex LH20; water) and then freeze dried to give the product as a fluffy white solid (86 mg).

EXAMPLE 24

Preparation of Sodium 4-(Phosphonomethyl) phenylthiourea Terminated Dendrimers

PAMAM 4.0 (EDA)

Solid sodium 4-(phosphonomethyl)phenylisothiocyanate (97 mg) was added to a solution of PAMAM 4.0 (EDA) (69 mg; 0.01 mmol) in water (30 ml). The resulting solution was stirred for 3 days at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (102 mg).

EXAMPLE 25

Preparation of Sodium Ethyl 4-(Phosphonomethyl) phenylthiourea Terminated Dendrimers

PAMAM 4.0 (EDA)

Solid sodium ethyl 4-(phosphonomethyl) phenylisothiocyanate (109 mg) was added to a solution of PAMAM 4.0 (EDA) (69 mg; 0.01 mmol) in DMF (30 ml). The resulting solution was stirred for 17 hours at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (30 mg).

EXAMPLE 26

Preparation of $C_n$-alkyl Linked 2-Thiosialoside Terminated Dendrimers

Methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate was prepared by the following procedure.

To a solution of methyl 5-acetamido4,7,8,9-tetra-O-acetyl-2-S-acetyl-3,5-dideoxy-2-thio-D-glycero-α-D-galacto-2-nonulopyranosonate (Hasegawa et al, 1986) (100 mg.) in dry dimethylformamide (1 ml) was added 8-bromooctanoic acid (41 mg.) and diethylamine (280 mg.) and the solution stirred at 20° C. for 17 hours.

Solvent was removed under vacuum and the residue partitioned between ethyl acetate and ice cold 5% hydrochloric acid. The organic layer was washed with water, dried over sodium sulphate, and evaporated to give a residue (130 mg.). This was dissolved in ethyl acetate (5 ml.) and N-hydroxysuccinimide (26 mg.) and dicyclohexylcarbodiimide (46 mg.) were added. The mixture was stirred at 20° C. for 17 hours then the white precipitate was filtered off. The filtrate was concentrated and purified by flash chromatography on silica gel eluting with ethyl acetate. Fractions containing product were combined and evaporated to give a white foam 97 mg. 71%.

Similarly were prepared:

Methyl [(11-undecanoic acid N-hydroxysuccinimide ester) 5-acetanido-4,7,8,9-tetra-O-acetyl-3,5-dideoxy-2-thio-D-glycero-α-D-galacto-2-nonulopyranosid] onate.

Methyl [(acetic acid N-hydroxysuccinimide ester) 5-acetamido-4,7,8,9-tetra-O-acetyl-3,5-dideoxy-2-thio-D-glycero-α-D-galacto-2-nonulopyranosid]onate.

Methyl [(4-butanoic acid N-hydroxysuccinimide ester) 5-acetamido-4,7,8,9-tetra-O-acetyl-3,5-dideoxy-2-thio-D-glycero-α-D-galacto-2-nonulopyranosid]onate.

Methyl [(4-methylbenzoic acid N-hydroxysuccinimide ester) 5-acetamido-4,7,8,9-tetra-O-acetyl-3,5-dideoxy-2-thio-D-glycero-α-D-galacto-2-nonulopyranosid] onate.

A PAMAM [EDA] 4.0 [(8-Octanamido)-5-acetamido-3,5-dideoxy-2-thio-D-glycero-α-D-galacto-2-nonulopyranosidoic Acid]$_{32}$ BRI 6112

To a solution of the PAMAM [EDA] 4.0 (50 mg.) in dry dimethyl sulphoxide(4 ml.) under an inert atmosphere was added methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (300 mg.) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl [(8-Octanamido) 5-acetamido-4,7,8,9-tetra-O-acetyl-3,5-dideoxy-2-thio-D-glycero-α-D-galacto-2-nonulopyranosid]onate]$_{32}$ was obtained as a white powder. 182 mg. 93%

This was converted to the free sialoside by the following method:

To a solution of PAMAM [EDA] 4.0 [methyl [(8-octanamido) 5-acetamido-4,7,8,9-tetra-O-acetyl-3,5-dideoxy-2-thio-D-glycero-α-D-galacto-2-nonulopyranosid] onate]$_{32}$ (182 mg.) in dry methanol (3 ml.) under argon at 20° C. was added a freshly prepared 0.19 M solution of sodium methoxide in methanol (7 ml.) and the mixture stirred for 2.5 hours. The solvent was evaporated and the residue dissolved in water (10 ml.) and stirred for 3 hours. This solution was subjected to size exclusion chromatography on Sephadex LH20 eluting with water. On lyophilisation, the product, PAMAM [EDA] 4.0 [(8-octanamido)-5-acetamido-3,5-dideoxy-2-thio-D-glycero-α-D-galacto-2-nonulopyranosidoic acid]$_{32}$ was obtained as a pale lemon powder 110 mg. 77%

By a similar procedure were prepared:

PAMAM [EDA] 4.0 [(11-undecanamido)-5-acetamido-3,5-dideoxy-2-thio-D-glycero-α-D-galacto-2-nonulopyranosidoic acid]$_{32}$ BRI 6147

PAMAM [EDA] 4.0 [(acetamido)-5-acetamido-3,5-dideoxy-2-thio-D-glycero-α-D-galacto-2-nonulopyranosidoic acid]$_{32}$ BRI 6121

PAMAM EDA] 4.0 [(4-methylbenzamido)-5-acetamido-3,5-dideoxy-2-thio-D-glycero-α-D-galacto-2-nonulopyranosidoic acid]$_{32}$ BRI 6120

B BHA lyslys$_2$lys$_4$lys$_8$lys$_{16}$ [(8-Octanamido)-5-acetamido-3,5-dideoxy-2-thio-D-glycero-α-D-galacto-2-nonulopyranosidoic Acid]$_{32}$ BRI 6169

A solution of BHA lyslys$_2$lys$_4$lys$_8$lys$_{16}$ (t-Boc)$_{32}$ (20.3 mg.) in a mixture of trifluoroacetic acid (2 ml.) and dichloromethane (2 ml.) was stirred at 20° C. for 2 hours then solvent was removed under vacuum. The residue was dissolved in dry dimethyl sulphoxide (1 ml.) and di-isopropylethylamine (25 mg.) and methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (78 mg.) were added. The mixture was stirred under argon at 20° C. for 60 hours then solvent was removed under vacuum. The residue was dissolved in a freshly prepared 0.1M solution of sodium methoxide in methanol (2.5 ml.) and the mixture stirred for 3 hours under argon at 20° C. The solvent was evaporated and the residue dissolved in water (1 ml.) and stirred for 17 hours . This solution was subjected to size exclusion chromatography on Sephadex LH20 eluting with water. After lyophilisation, the product, BHA lyslys$_2$lys$_4$lys$_8$lys$_{16}$ [(8-octanamido)-5-acetamido-3,5-dideoxy-2-thio-D-glycero-α-D-galacto-2-nonulopyranosidoic acid]$_{32}$ was obtained as a white powder 44 mg. 86%.

EXAMPLE 27

Preparation of Dendritic Sialosides Modified in the 4-Position of Sialic Acid

Methyl 4-azido-5-acetamido-7,8,9-tri-O-acetyl-2-S-acetyl-3,4,5-trideoxy-2-thio-D-glycero-α-D-galacto-2-nonulopyranosonate was prepared by the following procedure. To a solution of methyl 4-azido-5-acetamido-7,8,9-tri-O-acetyl-2-chloro-3,4,5-trideoxy-D-glycero-β-D-galacto-2-nonulopyranosonate (Sabesan, 1994) (5 g.) in dry dichloromethane (150 ml.) was added finely powdered potassium thiolacetate (5.8 g.) and the suspension stirred vigorously at 20° C. for 48 hours. The mixture was filtered and evaporated to give a light brown foam (5.2 g.). The required product was isolated by preparative reversed phase HPLC [C$_{18}$, 30% acetonitrile/water] as a white foam 3.9 g. 72%.

Methyl [(8-octanoic acid N-hydroxysuccinimide ester) 4-azido-5-acetamido-7,8,9-tri-O-acetyl-3,4,5-trideoxy-2-thio-D-glycero-α-D-galacto-2-nonulopyranosid]onate was prepared by the following procedure.

To a solution of methyl 4-azido-5-acetamido-7,8,9-tri-O-acetyl-2-S-acetyl-3,4,5-trideoxy-2-thio-D-glycero-α-D-galacto-2-nonulopyranosonate (300 mg.) in dry dimethylformamide (3.5 ml.) was added 8-bromooctanoic acid (155 mg.) and diethylamine (1.26 ml.) and the solution stirred at 20° C. for 17 hours. Solvent was removed under vacuum and the residue partitioned between ethyl acetate and ice cold 10% hydrochloric acid. The organic layer was washed with water, dried over sodium sulphate, and evaporated to give a yellow foam (385 mg.). This was dissolved in ethyl acetate (20 ml.) and N-hydroxysuccinimide (95 mg.) and dicyclohexylcarbodiimide (175 mg.) were added. The mixture was stirred at 20° C. for 17 hours then the white precipitate was filtered off. The filtrate was concentrated and purified by preparative reversed phase HPLC [$C_{18}$, 30% acetonitrile/water] to give a white foam 340 mg. 83%.

A PAMAM [EDA] 4.0 [(8-Octanamido)-4-azido-5-acetamido-3,4,5-trideoxy-2-thio-D-glycero-α-D-galacto-2-nonulopyranosidoic Acid]$_{32}$ BRI 6146

To a solution of the PAMAM [EDA] 4.0 (72 mg.) in dry dimethyl sulphoxide (5 ml.) under an inert atmosphere was added methyl [(8-octanoic acid N-hydroxysuccinimide ester) 4-azido-5-acetamido-7,8,9-tri-O-acetyl-3,4,5-trideoxy-2-thio-D-glycero-α-D-galacto-2-nonulopyranosid]onate (318 mg) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl [(8-octanamido) 4-azido-5-acetamido-7,8,9-tri-O-acetyl-3,4,5-trideoxy-2-thio-D-glycero-α-D-galacto-2-nonulopyranosid]onate]$_{32}$ was obtained as a white foam. 225 mg. 81%

The free sialoside was obtained by the following method:

To a solution of PAMAM [EDA] 4.0 [methyl [(8-octanamido) 4-azido-5-acetamido-7,8,9-tri-O-acetyl-3,4,5-trideoxy-2-thio-D-glycero-α-D-galacto-2-nonulopyranosid]onate]$_{32}$ (215 mg.) in dry methanol (1 ml.) under argon at 20° C. was added a freshly prepared 1 M solution of sodium methoxide in methanol (1 ml.) and the mixture stirred for 3 hours. The solvent was evaporated and the residue dissolved in water (2 ml.) and stirred for 17 hours. This solution was subjected to size exclusion chromatography on Sephadex LH20 eluting with water. On lyophilisation, the product, PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ was obtained as a fluffy white powder 160 mg. 90%

PAMAM [EDA] 4.0 [(8-Octanamido)-4-amino-5-acetamido-3,4,5-trideoxy-2-thio-D-glycero-α-D-galacto-2-nonulopyranosidoic Acid]$_{32}$ BRI 6149

A slow steam of hydrogen sulphide gas was passed into a solution of PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ (25 mg.) in a mixture of pyridine (40 ml.) and water (20 ml.) at 20° C. for 5 days. The solution was then bubbled with nitrogen for 2 hours to remove excess hydrogen sulphide. The solution was evaporated to dryness and the residue taken up in water (5 ml) and filtered through a 0.45 µm. membrane filter to remove sulphur. On lyophilisation, the product, PAMAM [EDA] 4.0 [(8-octanamido)-4-amino-5-acetamido-3,4,5-trideoxy-2-thio-D-glycero-α-D-galacto-2-nonulopyranosidoic acid]$_{32}$ was obtained as a fluffy white powder 23 mg. 96%

EXAMPLE 28

Preparation of Boronic Acid Terminated Dendrimers

4-Carboxyphenylboronic Acid N-Hydroxysucciniimide Ester

To a solution of 4-carboxyphenylboronic acid (500 mg.) in dry dimethyl formamide (5 ml) were added N-hydroxysuccinimide (380 mg.) and dicyclohexylcarbodiimide (680 mg) The mixture was stirred at 20° C. for 64 hours then the white precipitate was filtered off. The solvent was removed under vacuum and the residue dissolve in ethyl acetate (100 ml.). This solution was washed with water, dried over sodium sulphate and evaporated to give a white solid which was crystallised from acetonitrile/water as fine needles 730 mg. 92%.

PAMAM [EDA] 4.0 [4-Benzamidoboronic Acid]$_{32}$ BRI 6160

To a solution of the PAMAM [EDA] 4.0 (69 mg.) in dry dimethyl sulphoxide (5 ml) under an inert atmosphere was added 4-carboxyphenylboronic acid N-hydroxysuccinimide ester (130 mg.) and the solution stirred for 65 hours at 20° C. To the thick slurry was added 1M sodium carbonate solution (1 ml.) and the clear solution stirred an additional 24 hours. The solvent was removed under vacuum and the residue was dissolved in 10% ammonia solution (5 ml.). This solution was subjected to size exclusion chromatography on Sephadex LH20 eluting with 10% ammonia solution. On evaporation of solvent, the product, PAMAM [EDA] 4.0 [4-benzamidoboronic acid]$_{32}$ was obtained as a white fluffy solid. 110 mg. 94%.

EXAMPLE 29

Preparation of Sodium 3,6-Disulfonaphthylthiourea Terminated Dendrimers

BHAlyslys$_2$lys$_4$lys$_8$lys$_{16}$lys$_{32}$

Trifluoroacetic acid (2 ml) was added to a stirred suspension of BHAlyslys$_2$lys$_4$lys$_8$lys$_{16}$DBL$_{32}$ (147 mg) in dry dichloromethane (2 ml) and the resulting solution stirred at room temperature under nitrogen for two hours and then concentrated. The residue was dissolved in N,N-dimethyl-N-allylamine buffer (pH 9.5; 5 ml) and then solid 3,6-disulfonaphthyl isothiocyanate (400 mg) added. The pH of the mixture was then adjusted to 9.5 by the addition of 1M sodium carbonate and the solution heated at 53° C. for three hours under nitrogen. The reaction mixture was concentrated and the residue redissolved in water and the solution passed through a column of Amberlite IR 120 (Na). The filtrate was concentrate was concentrated to give the crude product, which was purified by gel filtration (Sephadex LH20; water) to give BHAlyslys$_2$lys$_4$lys$_8$lys$_{16}$lys$_{32}$ with 64 sodium 3,6-disulfonaphthylurea groups as a white fluffy solid (175 mg).

EXAMPLE 30

Preparation of Sodium 3,5-Disulfophenylthiourea Terminated Dendrimers

BHAlyslys$_2$lys$_4$lys$_8$lys$_{16}$lys$_{32}$

Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (187 mg). The oil was dissolved in a 1:1 mixture of pyridine/water (8 ml) and solid sodium 3,5-disulfophenyl isothiocyanate (680 mg; 2 mmol) added. The resulting solution was heated at 53° C. for three hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-disulfophenylurea groups as a white fluffy solid.

EXAMPLE 31

Preparation of Sodium 3,5-Dicarboxyphenylthiourea Terminated Dendrimers

BHAlyslys$_2$lys$_4$lys$_8$lys$_{16}$lys$_{32}$ BRI 6741

Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (186 mg). The oil was dissolved in a 1:1 mixture of pyridine/water (8 ml) and sodium 3,5-dicarboxyphenyl isothiocyanate (450 mg; 2 mmol) added. The resulting solution was heated at 53° C. for 13 hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-dicarboxyphenylurea groups as a fluffy solid.

The corresponding sodium 3,5-dicarboxyphenylthiourea terminated dendrimer PAMAM 4.0 (EDA) BRI 6195 was similarly prepared.

EXAMPLE 32

Preparation of Sodium 4-Phosphonooxyphenylthiourea Terminated Dendrimers

BHAlyslys$_2$lys$_4$lys$_8$lys$_{16}$lys$_{32}$ BRI 6181

Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonooxyphenyl isothiocyanate (250 mg) added. The pH of the resulting solution was adjusted to 10 with 1M sodium carbonate and the mixture heated at 53° C. for three hours under nitrogen. The solution was then concentrated to give a white solid residue. The residue was redissolved in water and the solution passed through a column of Amberlite IR 120 (Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonooxyphenylurea groups as a white fluffy solid (150 mg).

EXAMPLE 33

Preparation of Sodium 4-Phosphonophenylthiourea Terminated Dendrimers

BHAlyslys$_2$lys$_4$lys$_8$lys$_6$lys$_{32}$

Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonophenyl isothiocyanate (250 mg) added. The pH of the resulting solution was adjusted to 9 with saturated sodium bicarbonate solution and the mixture heated at 53° C. for three hours under nitrogen. The solution was then concentrated to give a white solid residue. The residue was redissolved in water and the solution passed through a column of Amberlite IR 120 Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonophenylurea groups BRI 6196 as a white fluffy solid (152 mg) after freeze drying.

EXAMPLE 34

Preparation of Sodium 4,6-Diphosphononaphthylthiourea Terminated Dendrimers

PAMAM 4.0

A solution of sodium 4,6-diphosphononaphthyl isothiocyanate (165 mg) in water (2 ml) was added to a solution of PAMAM 4.0 (51 mg; 0.01 mmol) in water (2 ml). The pH of the mixture was adjusted to 9.5 with saturated sodium bicarbonate solution and the mixture vigorously stirred for one hour at room temperature and then heated at 53° C. for three hours under nitrogen. The mixture was then filtered and the filtrate concentrated to give a brown solid residue. The crude product was purified by gel filtration (Sephadex G25; water) to give PAMAM 4.0 terminated with 24 sodium 4,6-diphosphononaphthylthiourea groups as a brown solid (81 mg) after freeze drying.

EXAMPLE 35

Preparation of Fluoresceinthiourea Terminated Dendrimers

PAMAM 4.0 (EDA)

Solid fluorescein isothiocyanate (188 mg) was added to a solution of PAMAM 4.0 (EDA) (74 mg; 0.01 mmol) in water (3 ml). Saturated sodium bicarbonate solution was added to adjust the pH to 9 and the resulting homogenous solution stirred overnight at room temperature and then concentrated. The orange residue was purified by gel filtration (Sephadex LH20; water) to give PAMAM 4.0 (EDA) terminated with 21 fluoresceinthiourea groups as a fluffy orange solid (193 mg) after freeze drying.

EXAMPLE 36

Preparation of Sodium (Phenyl-3-boronic Acid)-thiourea Terminated Dendrimers

PAMAM 4.0 (EDA)

Solid (phenyl-3-boronic acid) isothiocyanate (100 mg; 0.5 mmol) was added to a solution of PAMAM 4.0 (EDA) (69 mg; 0.01 mmol) in water (5 ml). 1M sodium carbonate was added to the isothiocyanate dissolved (pH ca.10). The mixture was then heated at 53° C. for two hours under nitrogen, and then filtered and the filtrate concentrated to give a brownish solid residue. The crude product was purified by gel filtration (Sephadex LH20; water) to give PAMAM 4.0 (EDA) terminated with 32 (phenyl-3-boronic acid)thiourea groups as a white fluffy solid (87 mg) after freeze drying.

EXAMPLE 37

Preparation of Pyridinium Dodecyl Carboxamido-terminated Dendrimers

PAMAM 2.0 dendrimer. BRI-6807

PAMAM generation 2.0 core (0.0479 mmol; 50 mg) was evaporated from a 0.5 ml solution in MeOH and then re-dissolved in 10 ml of water. 1-N-pyridinium 12-dodecanoic acid bromide (0.14 g; 0.384 mmol), N-hydroxybenzotriazole hydrate [HOBT] (52 mg; 0.384 mmol); triethylamine (53 µl 0.384 mmol) and 1-(3-diethylaminopropyl-3-ethyl) carbodiimide. HCl[EDC] (74 mg; 0.384 mmol), were added to the solution. This reaction mixture was stirred overnight at room temperature. The volume was reduced to a third under reduced pressure and the solution was chromatographed on a LH20 column using water as the eluent. Fractions containing the product were collected and pyridinium dodecylcarboxamide PAMAM 2.0 bromide isolated as a fluffy white solid by freeze drying. $^1$H nmr (D$_2$O): δ 1.15, 1.45, 1.9, 2.15, 2.75, 2.8, 3.15, 3.35, 3.5, 4.55, 8.05, 8.5, 8,8.

PAMAM 4.0 dendrimer. BRI-6809.

PAMAM generation 4.0 core (0.05 mmol; 69 mg) was evaporated from a 1.0 ml solution in MeOH and then re-dissolved in 15 ml of water. 1-N-pyridinium 12-dodecanoic acid bromide (0.143 g; 0.4 mmol), N-hydroxybenzotriazole hydrate [HOBT] (77 mg; 0.4 mmol); triethylamine (56 µl 0.4 mmol) and 1-(3-diethylaminopropyl-3-ethyl carbodiimide. HCl [EDC] (77 mg; 0.4 mmol) were added to the solution. This reaction mixture was stirred overnight at room temperature. The volume was reduced to a third under reduced pressure and the solution was chromatographed on a LH20 column using 1% triethylamine in water as the eluent. Fractions containing the product were collected and the pyridinium dodecylcarboxamide PAMAM 4.0 bromide was isolated as fluffy white solid by freeze drying. A small amount of the product was reacted with acetic anhydride to confirm the complete capping of the NH$_2$ end groups of the dendrimer core. $^1$H nmr (D$_2$O): δ 1.10, 1.45, 1.9, 2.1, 2.30, 2.5, 2.7, 3.2, 4.5, 8.00, 8.45, 8.80.

EXAMPLE 38

Preparation of Saccharin-terminated Dendrimers

PAMAM 4.0 Dendrimer BRI-6157

To a solution of ethylenediamine core PAMAM 4.0 dendrimer core (275 mg; 39.8 uM) in dry dimethyl formamide (25 ml) was added 6-(benzosulfimido) isothiocyanate (400 mg; 1.67 mM) and the mixture stirred at room temperature for 24 h. The cloudy solution was clarified by the adjustment of the pH with sodium carbonate solution to pH10–10.5. This solution was stirred for a further 24 h and volatiles removed on a rotary evaporator. The solution was chromatographed on a large Sephadex LH20 column and front fraction collected. The remaining fractions were collected and re-chromatographed on a smaller column. The combined front fractions were evaporated and freeze dried to yield the saccharin-terminated dendrimer product (450 mg; 78%) as a fluffy white solid. $^1$H nmr (D$_2$O): δ 2.20, 2.50 3.23, 3.46, 3.63, 7.52, 7.87.

The corresponding saccharin-terminated BHA.Lys.Lys$_2$.Lys$_4$.Lys$_8$.Lys$_{16}$.Lys$_{32}$ . . . dendrimer BRI-6189 was similarly prepared.

EXAMPLE 39

In vitro Anti Parasitic Assays

I: The following assay was performed as an in vitro assay to test for inhibition of trypanosomes.

A. Materials and Methods

Medium "Balz-MEM" plus 10% heat-inactivated horse serum.

Trypanosome strains STIB 900 (*T.b. rhodesiense* cloned from STIB 704)
STIB 920 (*T.b. brucei* cloned from STIB 348)
STIB 930 (*T.b. gambiense* cloned from STIB 754).

Standard drugs Melarsoprol (Arsobal, Specia, France), Pentamidine (Pentacarinat, Rhone-Poulenc), Suramin (Germnanin, Bayer, Germany).

Incubation conditions 72 hours at 37° C. and 5% CO$_2$ in a humid atmosphere.

Test system 96 well microtitre plate, 100 µl per well, 200–1000 trypanosomes per well (depending on the strain) and evaluation with two end point readings.

Evaluation a. By microscopical determination of the MIC
b. Fluorescent reading after BCECF/AM addition or counting the cells with Coulter Counter or CASY.

Drug preparation Stock solution of 10 mM in 10% solvent (DMSO, ethanol etc.), highest drug concentration is 50 µM.

Detailed Test Procedure The test is based on LILIT: Low Inoculum Long Incubation Test (Brun and Lun Vet. Par. 52 (1994) 37–46).

1. Add 50 µl of complete medium into wells of rows B–H, column numbers 2–10 of a 96 well plate (marked wells).
2. Add 75 µl of medium containing two times the highest drug concentration to be tested in wells B–D (D$_1$) and F–H (D$_2$) column number 11.
3. Prepare serial dilutions using a multipipette by transferring 25 µl from wells number 11 into wells number 10 and mix by sucking and dispensing medium a minimum of 10 times.
4. Continue with the dilution from right to left direction until 25 µl is added from well number 5 into well number 4. After mixing the remaining 25 µl is discarded. Wells number 2 and 3 in each row serve as control wells without drug.
5. Add 50 µl of trypanosome suspension into wells B, C and F, G numbers 2–11of the plate with a seeding density of 4×10$^3$/ml (makes 200/well). Add 50 µl of Baltz medium without trypanosomes to wells 2–11 of rows D and E as background controls for the fluorescence assay.
6. Incubate plate for 72 hours at 37° C., 5% CO$_2$.
7. Observe the plate under an inverted microscope to determine microscopically the MIC (Minimal Inhibitory Concentration): lowest drug concentration at which no trypanosome with normal morphology and motility as compared to control wells can be seen or the concentration at which no trypanosome survived.
8. The test can be further evaluated by fluorescence reading after the addition of BCECF/AM or by growth inhibition assessment by Coulter Counter.

B. Results

The following dendrimers were tested.

| BRI Number | MOL Name | Type of compound |
|---|---|---|
| BRI 2923 | PAMAM 4.0(NHCSNHNapth[SO$_3$Na]$_2$)$_{24}$ | dendrimer |
| BRI 2998 | PAMAM 4.0(NHCSNHNapth-3,6,8-triSO$_3$Na)$_{24}$ | dendrimer |
| BRI 6039 | PAMAM 4.0(NHCSNHN-1-Ph-3,5-[SO$_3$Na]$_2$)$_{24}$ | dendrimer |
| BRI 6041 | PAMAM 4.0(NHCOPhCH$_2$cyclam.4HCl)$_{32}$ | dendrimer |
| BRI 6042 | PAMAM 4.0(NHC = NHNH$_2$.HOAc)$_{24}$ | dendrimer |

(i) In vitro activity of 4 compounds tested against *T.b. rhodesiense* (STIB 900) in a 72 hr fluorescence assay. All compounds were dissolved in distilled water at a concentration of 4 mg/ml and then diluted to the desired concentration in complete cultivation medium.

| Compound | MTC (μg/ml) | MIC (μg/ml) | EC$_{50}$(μg/ml) |
|---|---|---|---|
| BRI 2998 | >100 | 3.7 | 7 |
|  | 333 | 4.1 | 6.3 |

MIC = minimum inhibition concentration (no trypanosomes alive)
MTC = maximum tolerated concentration (no drug effect).

(ii) In vitro activity of 5 compounds tested against *T.b. rhodesiense* (STIB 900) in a 72 hr fluorescence assay. All compounds were dissolved in distilled water at a concentration of 20 μg/ml and then diluted 1:10 in complete cultivation medium (BMEM plus 10% HI horse).

| Compound | MTC μg/ml | MTC μM | MIC μg/ml | MIC μM | EC$_{50}$ μg/ml | EC$_{50}$ μM |
|---|---|---|---|---|---|---|
| BRI 6042 | 666 | 87.7 | 74 | 9.7 | 120 | 15.8 |
| BRI 6041 | 666 | 62.3 | 74 | 6.9 | 190 |  |
| BRI 6039 | 1000 | 75.2 | 12.3 | 0.9 | 22 | 1.65 |
| BRI 2923 | >1000 | >70 | 37 | 2.5 | 170 |  |

II The following assay results were obtained in an in vitro assay to test for inhibition of Trypanosoma (T) and Plasmodium (P) species.

The following compounds were tested:

| BRI Number | MOL Name | |
|---|---|---|
| BRI 6157 | PAMAM 4.0 EDA(NHCSNH SaccharinNa)$_{32}$ | Polyamide amine core saccharin substituted dendrimer |
| BRI 6181 | BHAlys$_{31}$lys$_{32}$(NHCSNHPhOP[O][ONa]$_2$)$_{64}$ | Lysine core phenyl phosphate substituted dendrimer |
| BRI 6195 | PAMAM 4.0 EDA(NHCSNH-3,5 Ph [COOH]$_2$)$_{32}$ | Polyamide amine core phenyl carboxylate substitute dendrimer |

The tests were conducted using the following strains:

| Parasite | Strain | Stage | Standard |
|---|---|---|---|
| *T.b. rhodesiense* | STIB 900 | trypomastigotes | Melarsoprol |
| *P. falciparum* | NF54 | all | Chloroquine |

Results: (all values as μg/ml)

| Compound | *T.b. rhodesiense* MIC | *T.b. rhodesiense* IC-50 | *P. falciparum* IC-50 | Cytotoxicity MIC |
|---|---|---|---|---|
| BRI6157 | 33 | 5 | 22 | >100 |
| BRI6181 | >100 | >100 | 24 | >100 |
| BRI6195 | >100 | >100 | 20 | >100 |

EXAMPLE 40

Determination of Antibacterial Activity

Bacteria used in this assay were:
*Staphylococcus aureus* (ATCC 29213)
*Enterococcus faecalis* (ATCC29212)
*Escherichia coli* (ATCC 25922)

Minimum inhibitory concentrations (MIC) and minimum bactericidal concentrations (MBC) were determined by micro broth dilution (NCCLS-M7A3 1993) in Cation Adjusted Mueller-Hinton Broth (pH 7) using inoculum 2–5×10$^4$ cfu (log phase) and incubation for 24 and 48 h at 35° C., aerobically. MBC is taken as titre showing 3 log reduction of inoculum. The results are set out in the following table (all units in μg/ml).

| Test Compound | *S. aureus* | *E. faecalis* | *E. coli* |
|---|---|---|---|
| BRI-6807 | 32; (128) | >256 | 128 |
| BRI-6809 | 8; (8) | 128 (128) | >256 |

MIC=Minimum Inhibitory Concentration
(MBC)=Minimum Bactericidal Concentration

EXAMPLE 41

Quantification of the Effect of Dendrimers on Invasion and Growth of the Human Malaria Parasite *Plasmodium falciparum* in Human Red Blood Cells In Vitro Methods Malaria Parasites. 3D7 is a well characterised in vitro culture-adapted line of *P. falciparum*. The parasite undergoes repeating cycles of growth and replication within human red blood cells. The duration of each cycle is 48 hours beginning with young ring-stage parasites that mature through pigmented trophozoites (during the first 24 hours of the cycle) to segmented schizonts that burst to release infectious merozoites that rapidly invade fresh red cells. Newly invaded merozoites become ring forms and the cycle repeats.

Parasite culture and growth assays. *P. falciparum* (line 3D7) parasites were maintained in synchronous in vitro culture in freshly collected human red blood cells using well-established techniques. For invasion assays, red cells containing mature, pigmented trophozoites were purified by gelatin flotation then resuspended in fresh human red blood cells so that approximately one in every 200 red blood cells was parasitised (0.5% parasitaemia). Fresh culture media was then added to give a final red cell concentration of $2 \times 10^8$ red cells/ml.

Aliquots of the red cell suspension (each of 95 μl) were dispensed in duplicate into 96 well plates. 5 μl of parasite culture media containing either the test compound (BRI 2999; BRI 6741; BRI 2998; BRI 7011; BRI 6181) or PBS (control) was added to appropriate wells and the plates incubated at 37° C. and 1% $O_2$. Thin smears from each of the wells were made immediately (time=0) then subsequently after 24, 48 and 72 hours of culture. From each smear parasitaemia and stage of parasite maturation was quantified by microscopic examination of the smears after staining with Giemsa at pH 7.2. This allowed invasion, parasite development and subsequent re-invasion to be quantified. At each sampling time point, the culture media (either with or without compound) in the remaining wells was completely replaced.

The test compounds were first dissolved at 20 mg/ml in sterile isotonic phosphate-buffered saline (pH 7.2), then further diluted to make concentrated stock solutions ranging between 1 mg/ml and 200 μg/ml. Stock solutions were stored at 4° C. throughout the duration of an assay and diluted appropriately in parasite culture media when required.

Results

Figure 2:
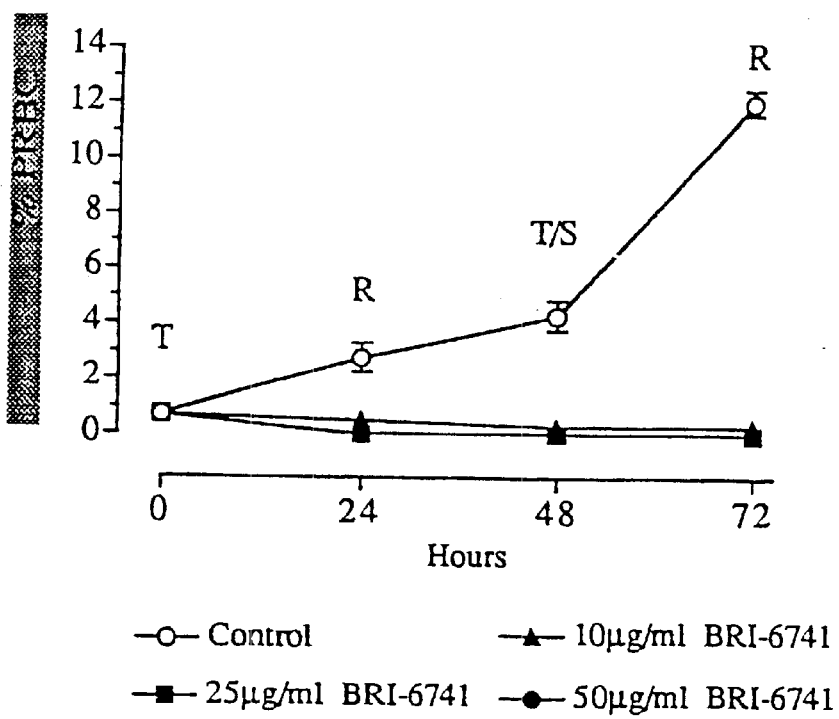
FIG. 2 shows the effect of BRI 6741 on growth of P. falciparum in human red blood cells in vitro.
Figure 3:
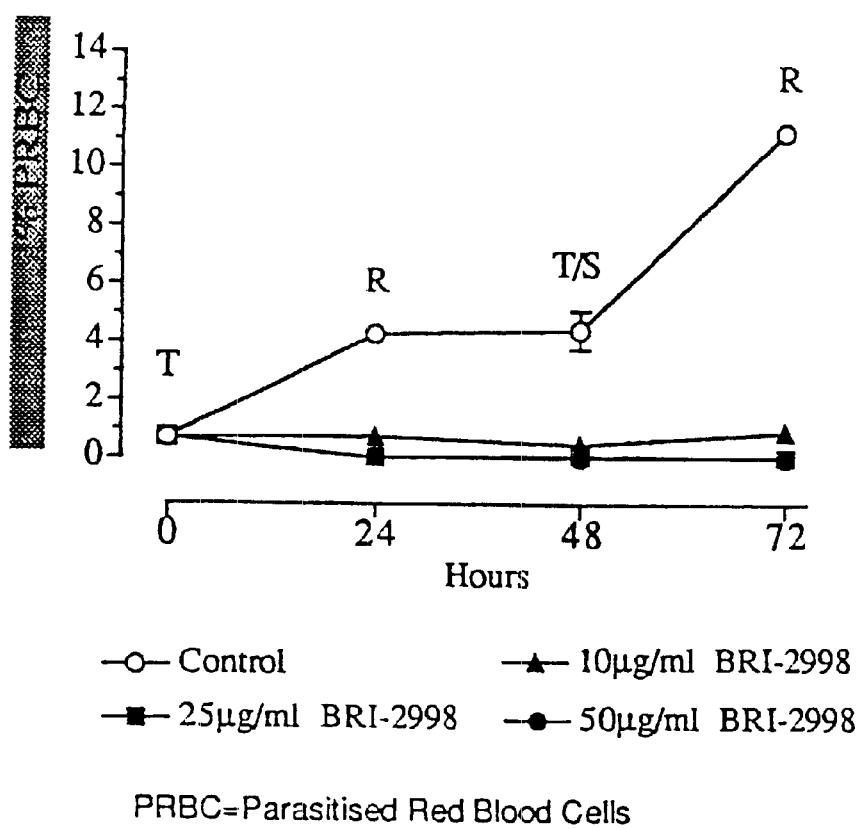
FIG. 3 shows the effect of BRI 2998 on growth of P. faiciparum in human red blood cells in vitro.
Figure 4:
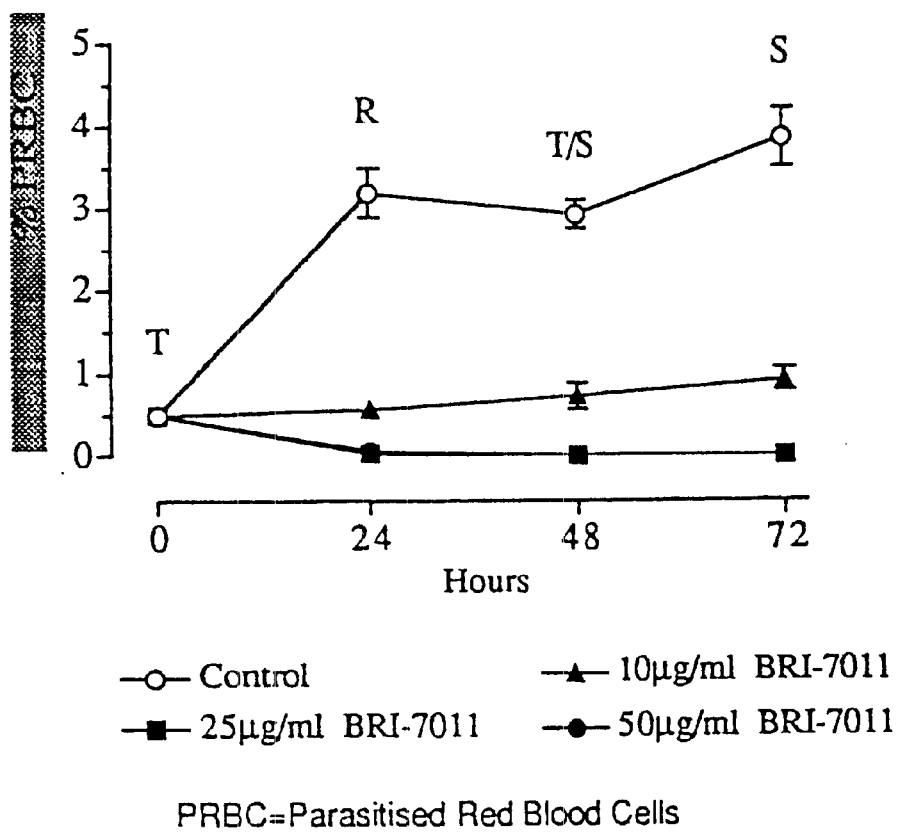
FIG. 4 shows the effect of BRI 7011 on growth of P. falciparum in human red blood cells in vitro.
Figure 5:
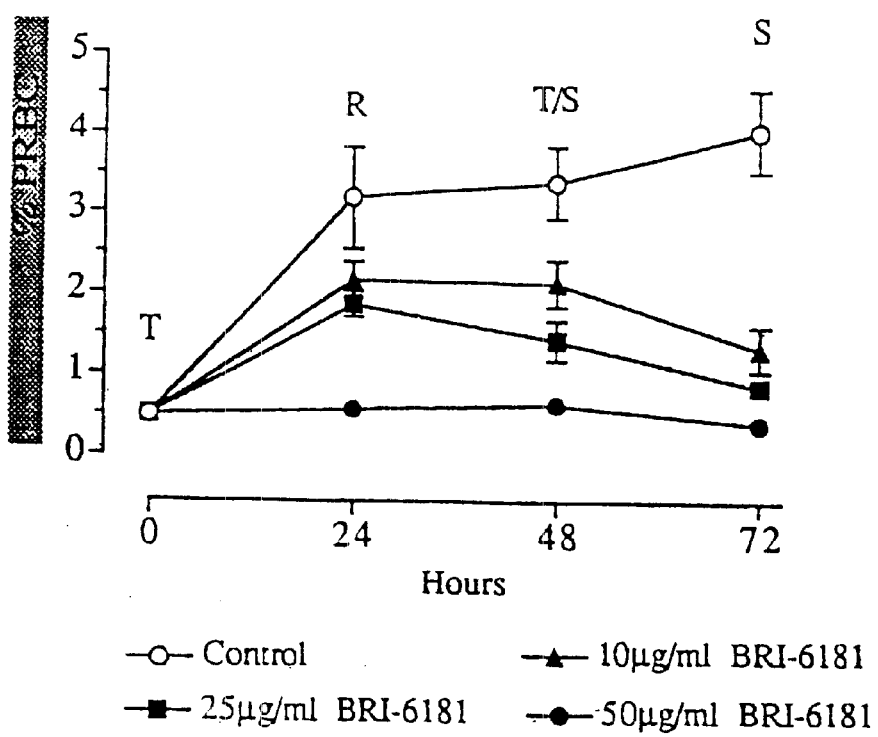
FIG. 5 shows the effect of BRI 6181 on growth of P. falciparum in human red blood cells in vitro.

Separate invasion/growth experiments were performed for each compound and the results are presented graphically in FIGS. 1 to 5. The effect of each compound was tested at final concentrations of 10, 25 and 50 μg/ml. Each of the five compounds showed a concentration-dependent inhibitory effect on parasite invasion, growth and replication, for any given concentration, the absolute level of inhibition did vary between the different compounds. At all concentrations tested (up to and including 50 μg/ml), none of the five test compounds had any obvious unfavourable effect on red blood cell morphology. In experiments in which BRI 7011 and BRI 6181 were tested (FIGS. 4 & 5), the level of re-invasion of parasites in control wells at 72 hours was lower than normally observed. This was due to an apparent retardation in parasite growth sometime after 48 hours of culture such that at 72 hours, a large proportion of the schizonts had not yet burst to release invasive merozoites.

What is claimed is:

1. A method of prophylactic or therapeutic inhibition of a bacterial, yeast, fungal, or protozoan in a human or non-human animal patient, which comprises administration to the patient of an effective amount of a dendrimer having a plurality of terminal groups wherein at least one of the terminal groups has an anionic- or cationic-moiety covalently bonded or linked thereto, said anionic-containing moiety is not a disaccharide or oligosaccharide moiety, and where said anionic-containing moiety is a neuraminic- or sialic acid-containing moiety, it is modified in the 4-position by substitution with an amino, amido, cyano, azido or guanido group, or is unsaturated.

2. A method according to claim 1, wherein said compound is a dendrimer which comprises a polyvalent core covalently bonded to at least two dendritic branches, and extends through at least two generations.

3. A method according to claim 2 wherein said dendrimer is a polyamidoamine dendrimer based on an ammonia core.

4. A method according to claim 2 wherein said dendrimer is a polyamidoamine dendrimer based on an ethylene diamine core.

5. A method according to claim 2 wherein said dendrimer is a polylysine dendrimer based on a benzhydrylamine or other suitable core.

6. A method according to claim 2 wherein said dendrimer is a poly(propyleneimine) dendrimer.

7. A method according to claim 2 wherein said compound is a polyionic dendrimer of the general formula I:

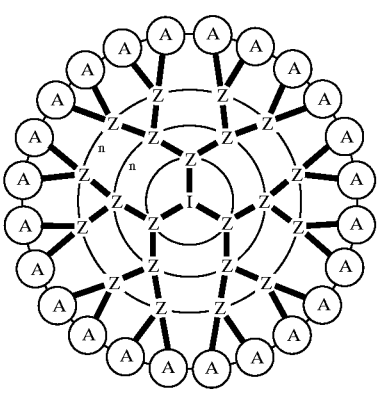

wherein:

I is an initiator core;

Z is an interior branching unit;

n is an integer which represents the number of generations of the dendrimer; and A is an anionic- or cationic-containing moiety, optionally linked to interior branching unit Z through a linking group X.

8. A method according to claim 1, wherein in said compound said anionic- or cationic-containing moiety or moieties are bonded to amine, sulfhydryl, hydroxy or other reactive terminal groups of the dendrimer by amide or thiourea linkages.

9. A method according to any claim 1, wherein in said compound said anionic- or cationic-containing moieties are selected from the group consisting of sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties), primary, secondary, tertiary or quaternary amino-containing moieties, pyridinium-containing moieties, guanidinium-containing moieties, amidinium-containing moieties, phenol-containing moieties, heterocycles possessing acidic or basic hydrogens, and zwitterionic-containing moieties.

10. A method according to claim 1, wherein in said compound the moiety or moieties which are bonded to amino or other reactive terminal groups of the dendrimer are selected from the following groups, in which n is zero or an integer of from 1 to 20:

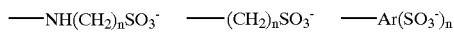
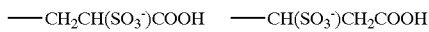
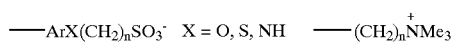

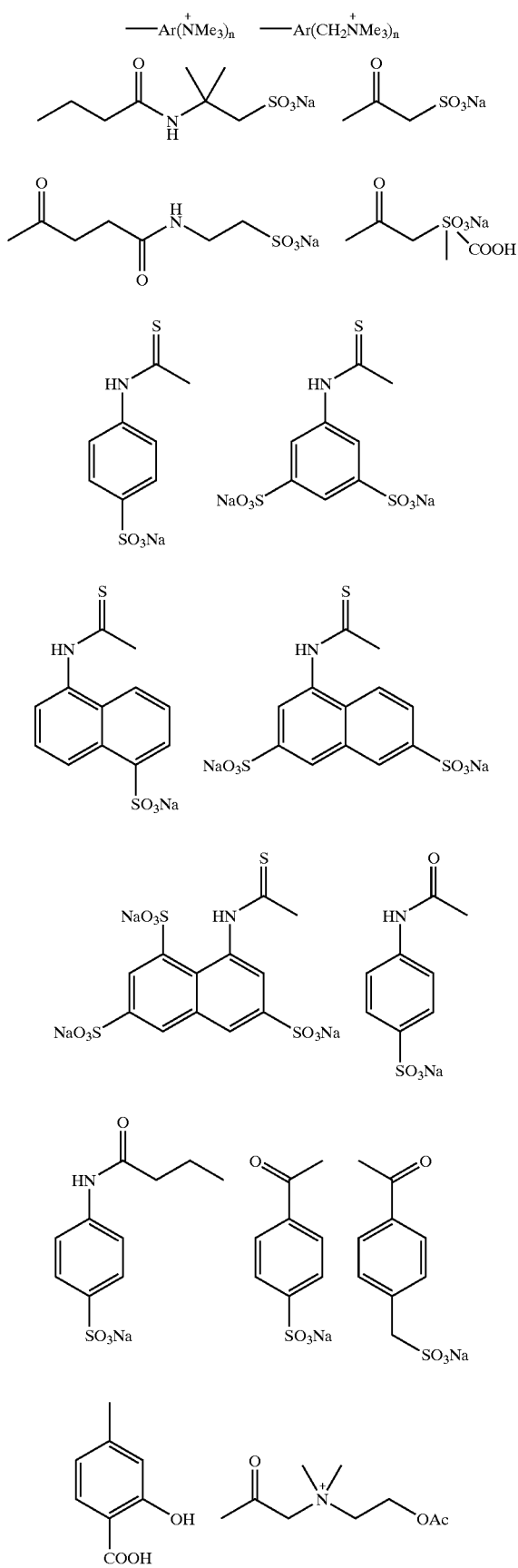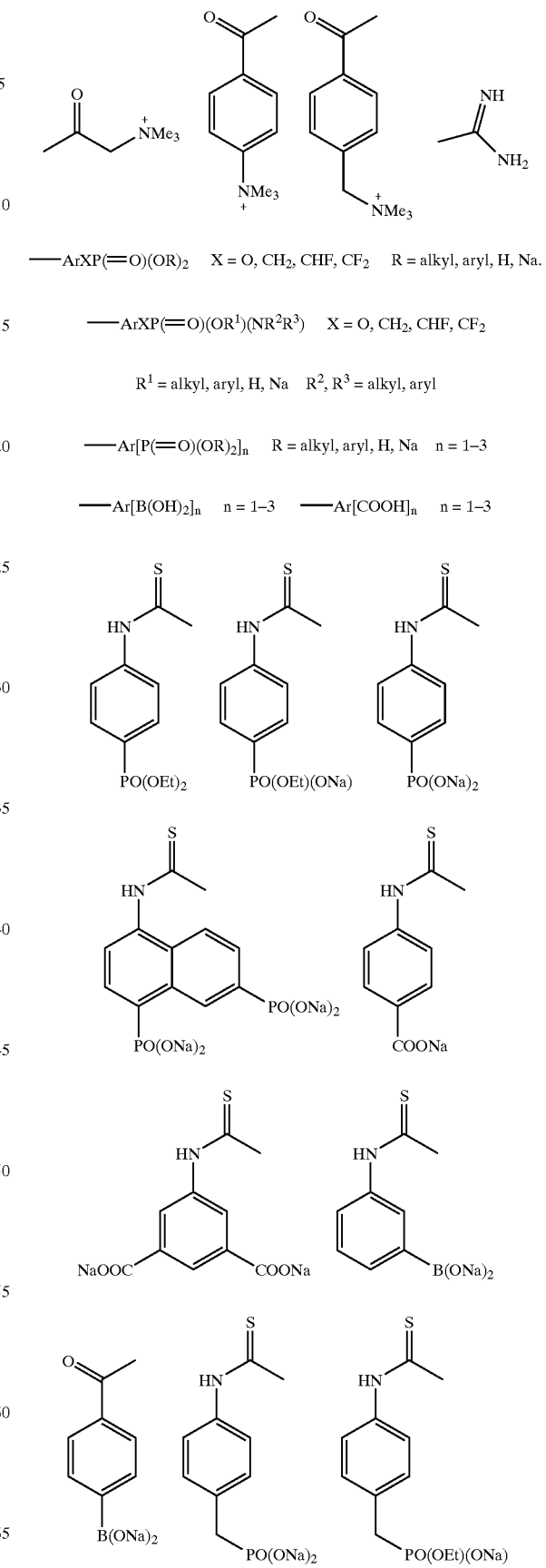

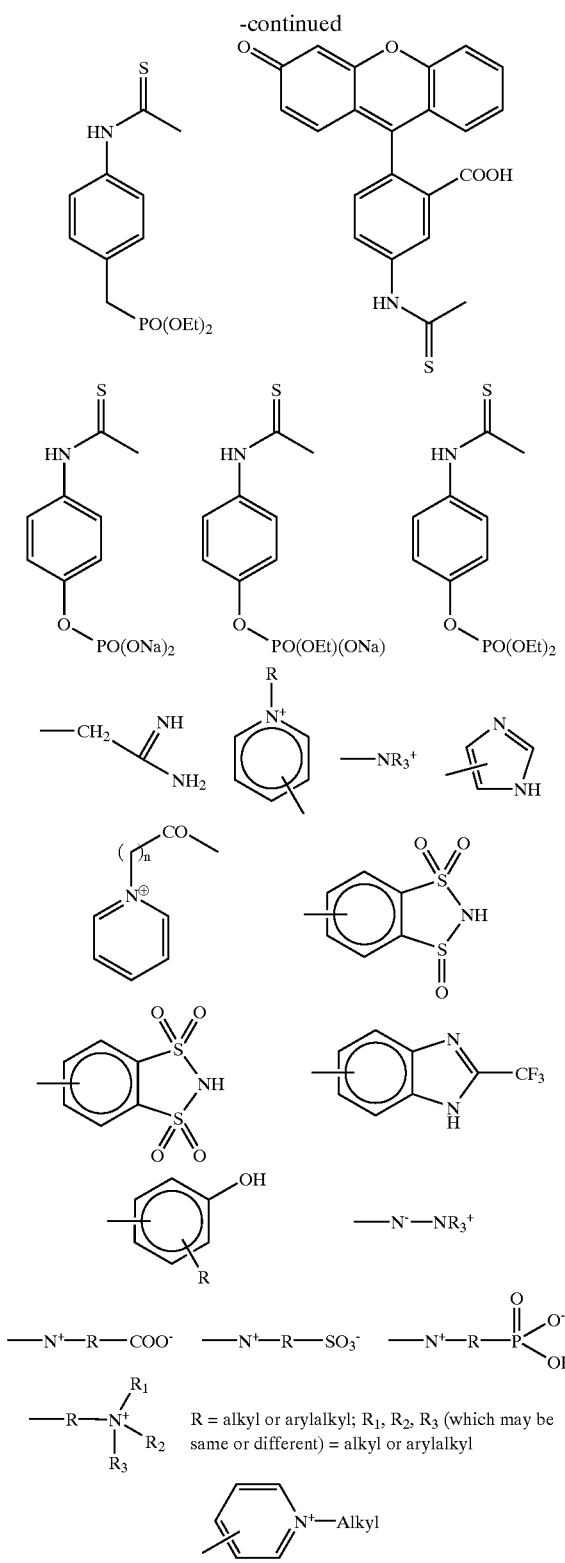

11. A method according to claim 1, wherein said compound is selected from the group consisting of:
  i. alkylsulfonic acid terminated dendrimers;
  ii. sulfoacetamide terminated dendrimers;
  iii. sulfosuccinamic acid terminated dendrimers;
  iv. N-(2-sulfoethyl) succinamide terminated dendrimers;
  v. 4-sulfophenylthiourea terminated dendrimers;
  vi. 3,6-di-sulfonaphthylthiourea terminated dendrimers;
  vii. 4-sulfonaphthylthiourea terminated dendrimers;
  viii. 3,5-di-sulfophenylthiourea terminated dendrimers;
  ix. 3,6,8-tri-sulfonaphthylthiourea terminated dendrimers;
  x. 4-(sulfomethyl) benzamide terminated dendrimers;
  xi. 4-sulfobenzamide terminated dendrimers;
  xii. N-(4-sulfophenyl) propanamide terminated dendrimers;
  xiii. 4-sulfophenylurea terminated dendrimers;
  xiv. N,N,N-tri-methylglycinamide terminated dendrimers;
  xv. 4-trimethylammonium benzamide terminated dendrimers;
  xvi. 4-(trimethylammoniummethyl)benzamide terminated dendrimers;
  xvii. N-(2-acetoxyethyl)-N,N-(dimethylammonium) methyl-carboxamide terminated dendrimers,
  xviii. guanidino terminated dendrimers;
  xix. 4-([1,4,8,11-tetraazacyclotetradecane]methyl) benzamide terminated dendrimers;
  xx. 4-carboxy-3-hydroxy-benzylamine terminated dendrimers;
  xxi. 4-carboxyphenylamide terminated dendrimers;
  xxii. 3,5-dicarboxyphenylamide terminated dendrimers;
  xxiii. 4-phosphonooxyphenylthiourea terminated dendrimers;
  xxiv. 4-(phosphonomethyl)phenylthiourea terminated dendrimers;
  xxv. ethyl-4-(phosphonomethyl)phenylthiourea terminated dendrimers;
  xxvi. (8-octanamido)-5-acetamido-3,5-dideoxy-2-thio-D-glycero-[]-D-galacto-2-nonulopyranosidoic acid terminated dendrimers;
  xxvii. (11-undecanamido)-5-acetamido-3,5-dideoxy-2-thio-D-glycero-[]-D-galacto-2-nonulopyranosidoic acid terminated dendrimers;
  xxviii. (acetamido)-5-acetamido-3,5-dideoxy-2-thio-D-glycero-[]-D-galacto-2-nonulopyranosidoic acid terminated dendrimers;
  xxix. (4-butanamido)-5-acetamido-3,5-dideoxy-2-thio-D-glycero-[]-D-galacto-2-nonulopyranosidoic acid terminated dendrimers;
  xxx. (4-methylbenzamido)-5-acetamido-3,5-dideoxy-2-thio-D-glycero-[]-D-galacto-2-nonulopyranosidoic acid terminated dendrimers;
  xxxi. (8-octanamido)-4-azido-5-acetamido-3,4,5-trideoxy-2-thio-D-glycero-[]-D-galacto-2-nonulopyranosidoic acid terminated dendrimers;
  xxxii. (8-octanamido)-4-amino-5-acetamido-3,4,5-trideoxy-2-thio-D-glycero-[]-D-galacto-2-nonulopyranosidoic acid terminated dendrimers;
  xxxiii. 4-benzamidoboronic acid terminated dendrimers;
  xxxiv. 3,5-dicarboxyphenylthiourea terminated dendrimers;
  xxxv. 4-phosphonooxyphenylthiourea terminated dendrimers;
  xxxvi. 4-phosphonophenylthiourea terminated dendrimers;
  xxxvii. 4,6-diphosphononaphthylthiourea terminated dendrimers;
  xxxviii. fluoresceinthiourea terminated dendrimers;

xxxix. (phenyl-3-boronic acid)-thiourea terminated dendrimers;

xi. pyridinium dodecylcarboxamide terminated dendrimers; and xii. saccharin terminated dendrimers.

12. A method according to claim 1, wherein said treatment comprises inhibition of bacterial, yeast or fungal pathogens, or parasitic pathogens.

* * * * *

UNITED STATES PATENT AND TRADEMARK OFFICE
CERTIFICATE OF CORRECTION

PATENT NO.    : 6,464,971 B1
DATED         : October 15, 2002
INVENTOR(S)   : Barry Ross Matthews and George Holan It is certified that error appears in the above-identified patent and that said Letters Patent is hereby corrected as shown below:

<u>Title page,</u>
Item [30], please change "5842/98" to -- PP5842/98 --.

Signed and Sealed this

Twenty-ninth Day of July, 2003

JAMES E. ROGAN
*Director of the United States Patent and Trademark Office*